United States Patent
Nicholas et al.

(10) Patent No.: US 10,446,342 B2
(45) Date of Patent: Oct. 15, 2019

(54) SURGICAL INSTRUMENTS AND SWITCH ASSEMBLIES THEREOF

(71) Applicant: Covidien LP, Mansfield, MA (US)

(72) Inventors: David Nicholas, Trumbull, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/973,956

(22) Filed: May 8, 2018

(65) Prior Publication Data

US 2018/0261409 A1    Sep. 13, 2018

Related U.S. Application Data

(63) Continuation of application No. 14/808,314, filed on Jul. 24, 2015, now Pat. No. 9,991,069.
(Continued)

(51) Int. Cl.
*A61B 17/00* (2006.01)
*H01H 13/14* (2006.01)
(Continued)

(52) U.S. Cl.
CPC ........... *H01H 13/14* (2013.01); *A61B 17/068* (2013.01); *A61B 17/07207* (2013.01);
(Continued)

(58) Field of Classification Search
CPC .... H01H 9/26; H01H 13/14; H01H 2300/014; A61B 17/068; A61B 2017/00017;
(Continued)

(56) References Cited

U.S. PATENT DOCUMENTS 4,196,348 A    4/1980 Iwakiri et al.
4,803,362 A    2/1989 Butts
(Continued)

FOREIGN PATENT DOCUMENTS

CN    101227187 A    7/2008
CN    203014768 U    6/2013
(Continued)

OTHER PUBLICATIONS

Chinese Office Action dated Nov. 22, 2018, corresponding to counterpart Chinese Application No. 201510689425.2; 13 total pages.
(Continued)

*Primary Examiner* — Vanessa Girardi

(57) ABSTRACT

A switch assembly includes a switch housing, a first switch subassembly, and a second switch subassembly. The first switch subassembly includes a shaft and a toggle button. The shaft is disposed within the switch housing and has a proximal end portion and a distal end portion. The shaft is pivotable relative to the switch housing about at least one pivot axis to actuate at least one function of a surgical instrument. The proximal end portion of the shaft includes a magnet. The toggle button is non-rotatably connected to the distal end portion of the shaft. The second switch subassembly includes a safety bar and a post. The safety bar is axially movable within the switch housing. The post extends through the safety bar such that movement of the safety bar along a longitudinal axis thereof moves the post between a firing position and a non-firing position.

20 Claims, 17 Drawing Sheets

Related U.S. Application Data

(60) Provisional application No. 62/066,996, filed on Oct. 22, 2014.

(51) Int. Cl.
*H01H 9/26* (2006.01)
*A61B 17/068* (2006.01)
*A61B 17/072* (2006.01)

(52) U.S. Cl.
CPC ..... *H01H 9/26* (2013.01); *A61B 2017/00017* (2013.01); *A61B 2017/0046* (2013.01); *A61B 2017/00367* (2013.01); *A61B 2017/00371* (2013.01); *A61B 2017/00389* (2013.01); *A61B 2017/00393* (2013.01); *A61B 2017/00398* (2013.01); *A61B 2017/00734* (2013.01); *H01H 2300/014* (2013.01)

(58) Field of Classification Search
CPC .......... A61B 2017/00367; A61B 2017/00389; A61B 2017/00393; A61B 2017/00371; A61B 2017/00398; H03K 17/97; H03K 17/9706; H03K 2017/9713; G05G 9/047; G05G 9/04707
See application file for complete search history.

(56) References Cited

U.S. PATENT DOCUMENTS

| | | | |
|---|---|---|---|
| 5,321,311 A | 6/1994 | Umemura et al. | |
| 5,747,953 A | 5/1998 | Philipp | |
| 5,903,257 A * | 5/1999 | Nishiumi ................ | A63F 13/02 345/156 |
| 6,013,991 A | 1/2000 | Philipp | |
| 6,025,683 A | 2/2000 | Philipp | |
| 6,517,565 B1 | 2/2003 | Whitman et al. | |
| 6,960,894 B2 | 11/2005 | Carusillo et al. | |
| 7,638,958 B2 | 12/2009 | Philipp et al. | |
| 7,821,500 B2 * | 10/2010 | Wedel .................. | H04M 1/233 345/156 |
| 8,480,703 B2 | 7/2013 | Nicholas et al. | |
| 8,968,276 B2 | 3/2015 | Zemlok et al. | |
| 9,307,986 B2 | 4/2016 | Hall et al. | |
| 9,326,767 B2 | 5/2016 | Koch, Jr. et al. | |
| 9,358,003 B2 | 6/2016 | Hall et al. | |
| 9,398,911 B2 | 7/2016 | Auld | |
| 9,468,438 B2 | 10/2016 | Baber et al. | |
| 9,554,794 B2 | 1/2017 | Baber | |
| 9,597,104 B2 | 3/2017 | Nicholas et al. | |
| 9,654,050 B2 | 5/2017 | Kokinelis | |
| 9,700,309 B2 | 7/2017 | Jaworek | |
| 9,700,318 B2 | 7/2017 | Scirica et al. | |
| 9,775,610 B2 | 10/2017 | Nicholas et al. | |
| 9,782,169 B2 | 10/2017 | Kimsey | |
| 9,782,187 B2 | 10/2017 | Zergiebel | |
| 9,801,646 B2 | 10/2017 | Zergiebel | |
| 9,991,069 B2 | 6/2018 | Nicholas et al. | |
| 2009/0095790 A1 | 4/2009 | Whitman et al. | |
| 2010/0171026 A1 | 7/2010 | Saitou et al. | |
| 2011/0121049 A1 | 5/2011 | Malinouskas et al. | |
| 2011/0204119 A1 | 8/2011 | McCuen | |
| 2012/0089131 A1 | 4/2012 | Zemlok et al. | |
| 2012/0130420 A1 | 5/2012 | Nicholas | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2015/0235789 A1 | 8/2015 | Calderoni | |
| 2015/0374372 A1 | 12/2015 | Zergiebel et al. | |

FOREIGN PATENT DOCUMENTS

| | | |
|---|---|---|
| CN | 103989496 A | 8/2014 |
| CN | 104042271 A | 9/2014 |
| KR | 20020020332 A | 3/2002 |
| KR | 20070000199 U | 2/2007 |
| WO | 2008147415 A1 | 12/2008 |

OTHER PUBLICATIONS

European Search Report, dated Feb. 25, 2016, corresponding to European Application No. 15190752.4; 8 pages.

* cited by examiner

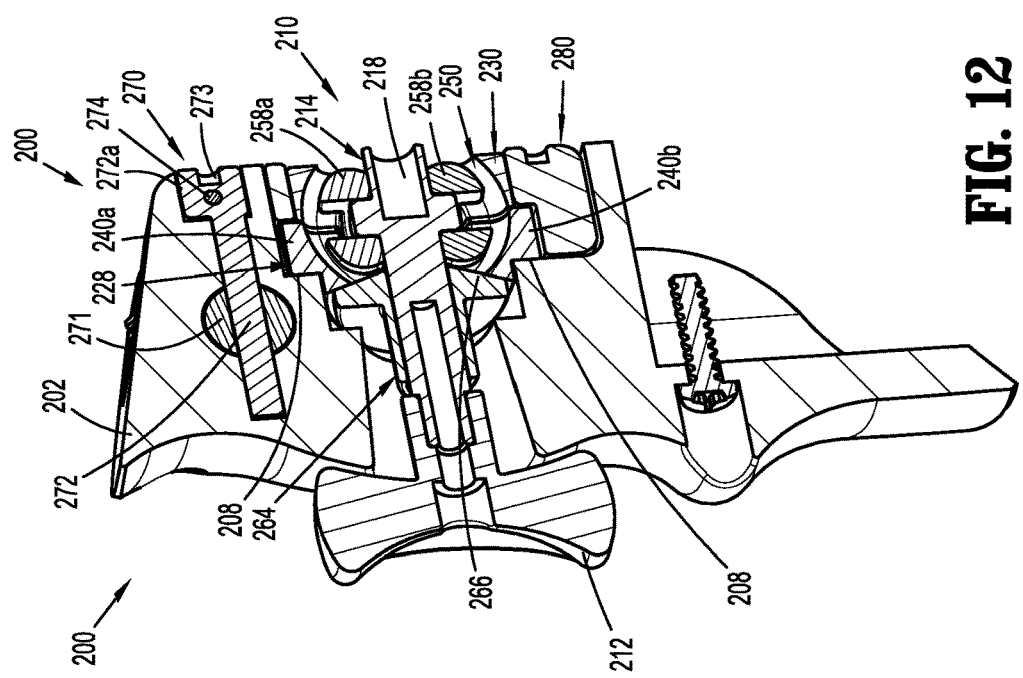
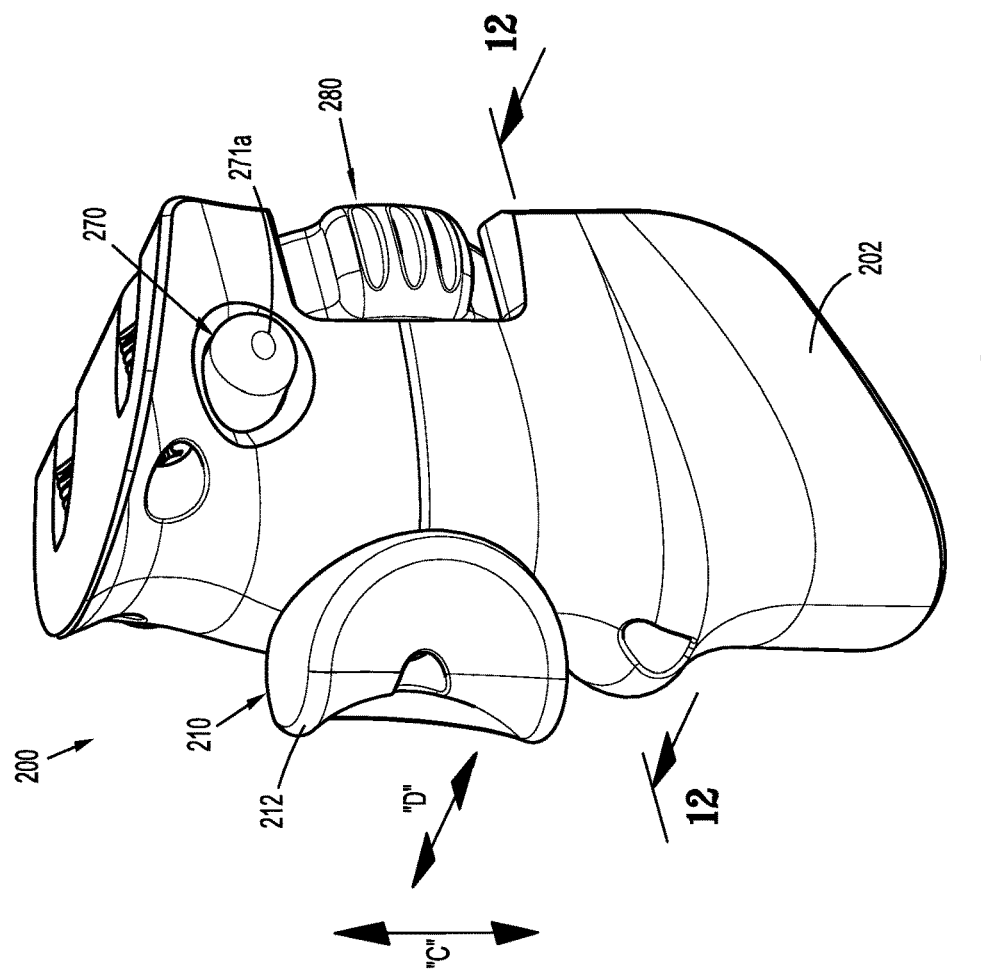

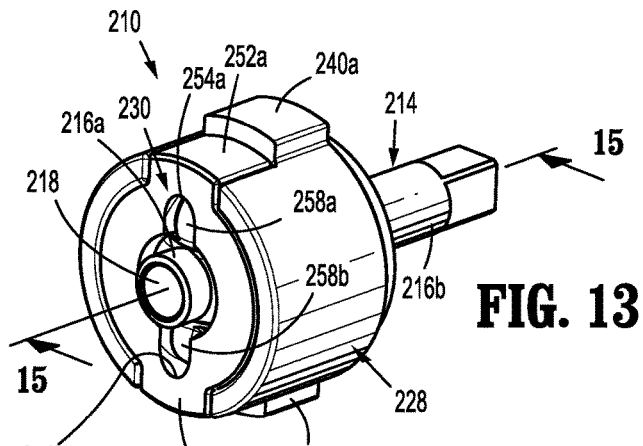
FIG. 13
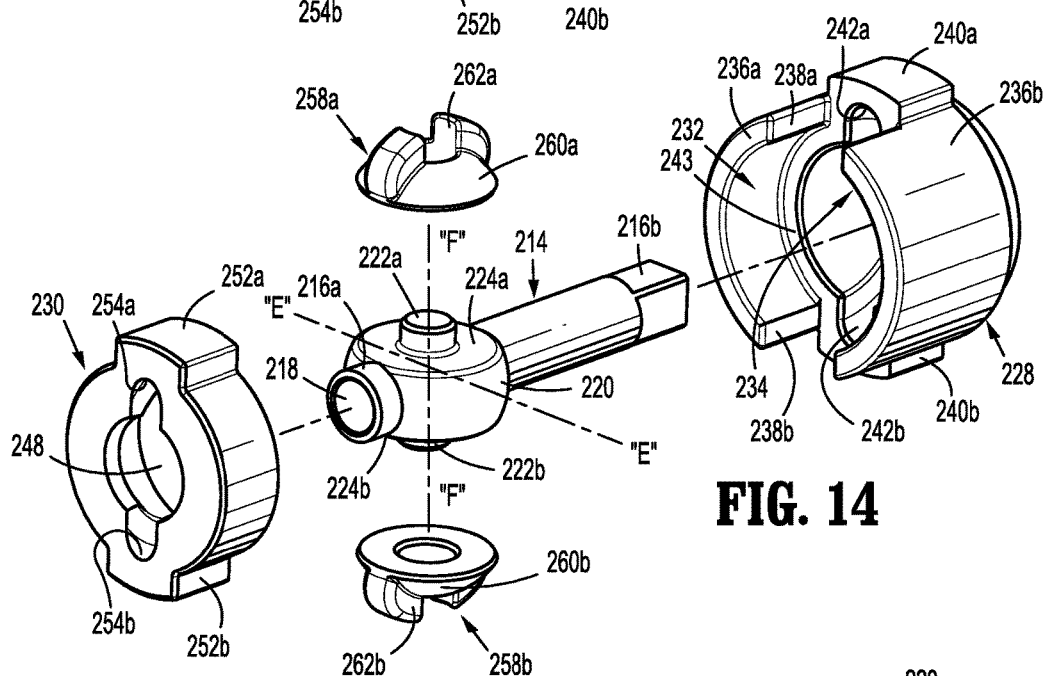
FIG. 14
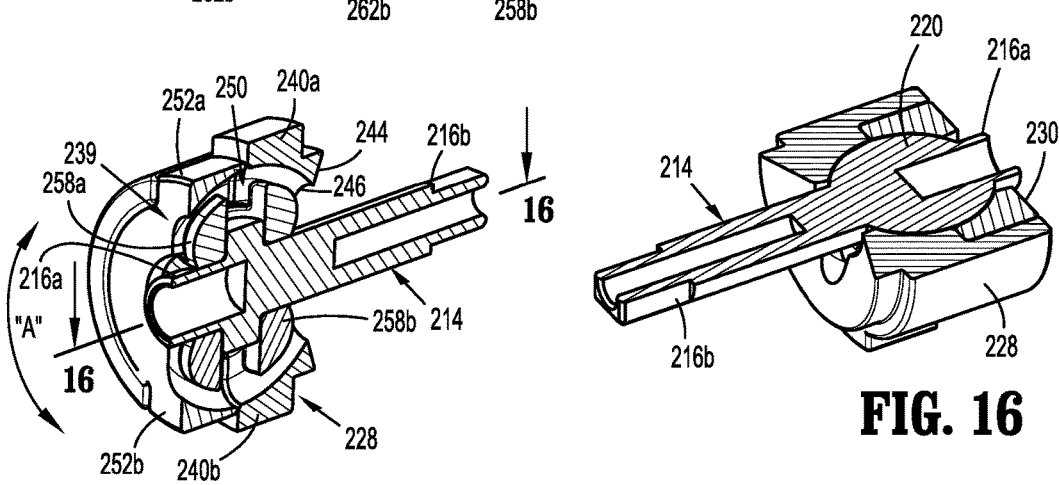
FIG. 15
FIG. 16

SURGICAL INSTRUMENTS AND SWITCH ASSEMBLIES THEREOF

CROSS-REFERENCE TO RELATED APPLICATIONS

This application is a Continuation Application of U.S. patent application Ser. No. 14/808,314, filed on Jul. 24, 2015, which claims the benefit of and priority to U.S. Provisional Patent Application No. 62/066,996, filed on Oct. 22, 2014, the entire contents of each of which being incorporated by reference herein.

BACKGROUND

1. Technical Field

The present disclosure relates to surgical instruments. More specifically, the present disclosure relates to switch assemblies for use with hand-held electromechanical surgical instruments to actuate various functions of surgical attachments, such as, for example, end effectors. Hand-held electromechanical surgical instruments and adapter assemblies for connecting surgical end effectors to handle assemblies are also described.

2. Background of Related Art

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

Handle assemblies include various switches used to actuate one or more functions of a surgical end effector. It is desirable for switches to be intuitive to operate, ergonomic in design, and capable of actuating a variety of independent functions of hand-held electromechanical surgical instruments.

SUMMARY

In one aspect of the present disclosure, a switch assembly for actuating functions of a hand-held surgical instrument is provided. The switch assembly includes a switch housing, a first switch subassembly, and a second switch subassembly. The switch housing defines a channel therethrough and a longitudinal axis. The first switch subassembly includes a shaft and a toggle button. The shaft is disposed within the channel of the switch housing and has a proximal end portion and a distal end portion. The shaft is pivotable relative to the switch housing about at least one pivot axis to actuate at least one function of a surgical instrument. The proximal end portion of the shaft includes a magnet. The toggle button is non-rotatably connected to the distal end portion of the shaft. The second switch subassembly includes a safety bar and a post. The safety bar extends through the switch housing, transverse to the longitudinal axis, and is axially movable therein. The safety bar has a first end and a second end and defines a longitudinal axis therebetween. The post extends through the safety bar, transversely thereto, such that movement of the safety bar along the longitudinal axis thereof moves the post between a firing position and a non-firing position.

In some embodiments, the shaft of the first switch subassembly may be pivotable relative to the switch housing about another pivot axis to actuate another function of a surgical instrument.

It is contemplated that the first switch subassembly may further include an outer member and an inner member. The outer member is disposed within the channel of the switch housing and is prevented from moving distally relative to the switch housing. The inner member may be non-rotatably disposed within the outer member. The shaft of the first switch subassembly may extend through the outer and inner members. The outer and inner members may define a cavity therein having a substantially spherical configuration. The proximal end portion of the shaft may have a spherical portion disposed in the spherical cavity.

It is envisioned that the first switch subassembly may further include a first keyed member and a second keyed member. The first keyed member may be rotatably connected to the spherical portion of the shaft. The second keyed member may be rotatably connected to the spherical portion of the shaft such that the keyed members resist rotation of the shaft about a longitudinal axis defined by the shaft.

In some aspects, the first switch subassembly may further include a pivoting member and a biasing member. The pivoting member may have a cone-shaped proximal end in abutment with a concave face of the outer member. The biasing member may be disposed between the cone-shaped proximal end of the pivoting member and the toggle button to center the toggle button within the channel.

In some embodiments, a proximal end of the post of the second switch subassembly may include a magnet configured to communicate with a hall effect sensor of a surgical instrument.

It is contemplated that the switch assembly may further include a third switch subassembly including an annular switch rotatably disposed within the switch housing to actuate at least one function of a surgical instrument.

In another aspect of the present disclosure, a handle assembly of a hand-held surgical instrument is provided. The handle assembly includes a handle housing, a plurality of motors disposed within the handle housing, a plurality of hall effect sensors, and a switch assembly. The hall effect sensors are disposed within the handle housing and in communication with the plurality of motors to actuate at least one of the plurality of motors. The switch assembly is supported on the handle housing and includes a switch housing, a first switch subassembly, and a second switch subassembly. The switch housing defines a channel therethrough and a longitudinal axis. The first switch subassembly includes a shaft and a toggle button. The shaft is disposed within the channel of the switch housing and has a proximal end portion and a distal end portion. The proximal end portion includes a magnet disposed adjacent a first hall effect sensor of the plurality of hall effect sensors. The shaft is pivotable relative to the switch housing about at least one pivot axis to signal the first hall effect sensor. The toggle button is non-rotatably connected to the distal end portion of the shaft. The second switch subassembly includes a safety bar and a post. The safety bar extends through the switch housing, transverse to the longitudinal axis, and is axially movable therein. The safety bar has a first end and a second end and defines a longitudinal axis therebetween. The post extends through the safety bar, transversely thereto. The post has a proximal end including a magnet in communication with a second hall effect sensor of the plurality of hall effect sensors such that movement of the safety bar along the longitudinal axis thereof moves the post between a firing position, in which a first motor of the plurality of motors is actuatable by the first switch subassembly, and a non-firing position, in which the first motor of the plurality of motors is prevented from actuation by the first switch subassembly.

In some embodiments, the handle assembly may further include a printed circuit board disposed within the handle housing. The printed circuit board may have the plurality of hall effect sensors arranged therealong. A battery may be coupled to the printed circuit board and electrically coupled to the plurality of motors.

It is contemplated that the handle assembly may further include a battery removably received within the handle housing and electrically coupled to the plurality of motors.

It is envisioned that an electrical cord may be electrically coupled to the plurality of motors.

In some aspects, the handle housing may include a distal half-section and a proximal half-section. The distal half-section may have the switch assembly secured thereto. The proximal half-section may be pivotably connected to the distal half section. The proximal half-section may have at least a portion of the plurality of motors disposed therein.

In yet another aspect of the present disclosure, a hand-held surgical instrument is provided. The surgical instrument includes a handle assembly and an adapter assembly. The handle assembly includes a handle housing, a plurality of motors disposed within the handle housing, a plurality of hall effect sensors, and a switch assembly. The hall effect sensors are disposed within the handle housing and in communication with the plurality of motors to actuate at least one of the plurality of motors. The switch assembly is supported on the handle housing and includes a switch housing, a first switch subassembly, and a second switch subassembly. The switch housing defines a channel therethrough and a longitudinal axis. The first switch subassembly includes a shaft and a toggle button. The shaft is disposed within the channel of the switch housing and has a proximal end portion and a distal end portion. The proximal end portion includes a magnet disposed adjacent a first hall effect sensor of the plurality of hall effect sensors. The shaft is pivotable relative to the switch housing about at least one pivot axis to signal the first hall effect sensor. The toggle button is non-rotatably connected to the distal end portion of the shaft. The second switch subassembly includes a safety bar and a post. The safety bar extends through the switch housing, transverse to the longitudinal axis, and is axially movable therein. The safety bar has a first end and a second end and defines a longitudinal axis therebetween. The post extends through the safety bar, transversely thereto. The post has a proximal end including a magnet in communication with a second hall effect sensor of the plurality of hall effect sensors such that movement of the safety bar along the longitudinal axis thereof moves the post between a firing position, in which a first motor of the plurality of motors is actuatable by the first switch subassembly, and a non-firing position, in which the first motor of the plurality of motors is prevented from actuation by the first switch subassembly. The adapter assembly includes a proximal end and a distal end. The proximal end has a plurality of rotatable shafts configured to be coupled to and driven by respective motors of the plurality of motors of the handle assembly. The distal end is configured to be operatively coupled to an end effector.

BRIEF DESCRIPTION OF THE DRAWINGS

Embodiments of the present disclosure are described herein with reference to the accompanying drawings, wherein:

FIG. 11 is a perspective view of the switch assembly of FIG. 10;

FIG. 12 is a cross-sectional view, taken along line 12-12 of FIG. 11, of the switch assembly;

FIG. 13 is a perspective view of a first switch subassembly of the switch assembly of FIG. 10;

FIG. 14 is a perspective view, with parts separated, of the first switch subassembly of FIG. 13;

FIG. 15 is a cross-sectional view, taken along line 15-15 of FIG. 13, of the first switch subassembly;

FIG. 16 is a cross-sectional view, taken along line 16-16 of FIG. 15, of the first switch subassembly;

DETAILED DESCRIPTION OF EMBODIMENTS

Figure 1B:
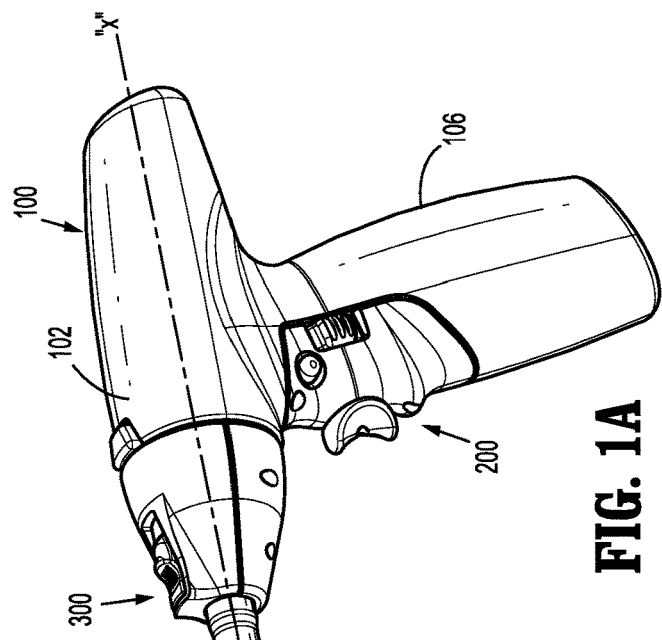
FIG. 1B is a perspective view of the handle assembly of FIG. 1A.

Embodiments of the presently disclosed surgical instruments including handle assemblies and switch assemblies thereof, adapter assemblies, and surgical end effectors are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

Figure 22:
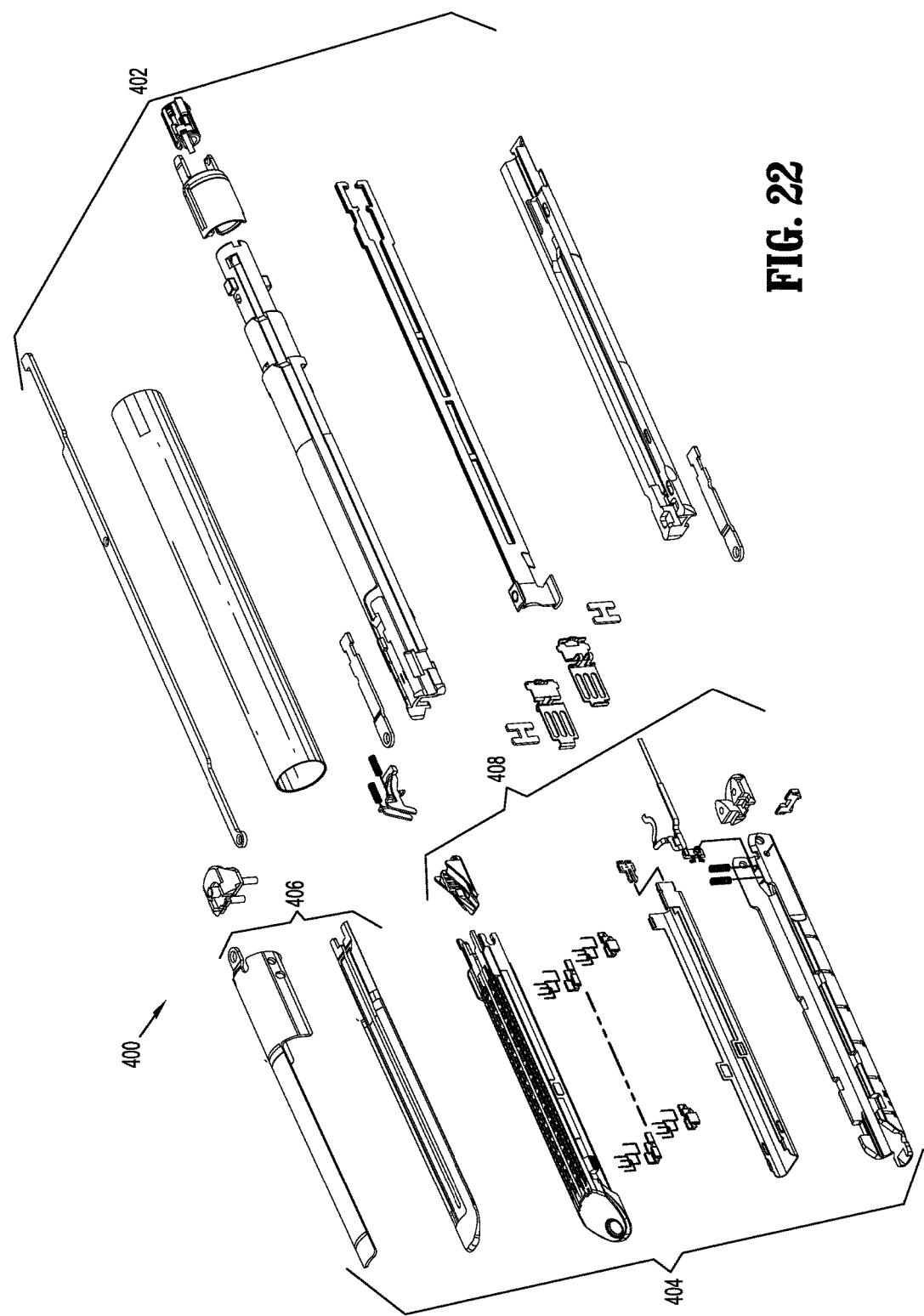
FIG. 22 is an exploded view of the surgical end effector of the hand-held electromechanical surgical instrument of FIG. 1A.

A surgical instrument, in accordance with an embodiment of the present disclosure, is generally designated as 10, and is in the form of a powered hand-held electromechanical surgical instrument configured for selective coupling thereto of a plurality of different surgical end effectors, for example, surgical end effector 400 (FIG. 22). The end effectors may be for any type of surgical instrument including, but not limited to, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, and a fluid delivery device. Each of the end effectors is configured for actuation and manipulation by the powered hand-held electromechanical surgical instrument 10.

Figure 1A:
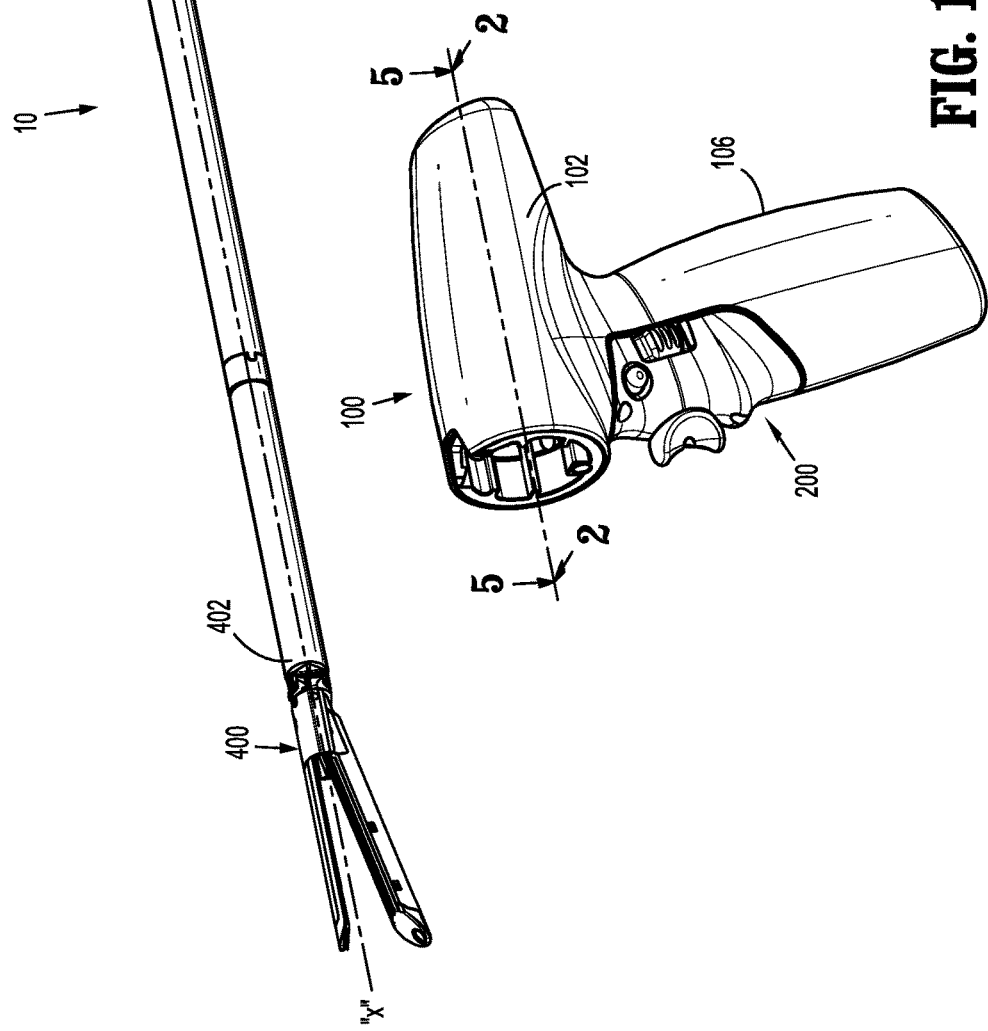
FIG. 1A is a perspective view of a hand-held electromechanical surgical instrument, including a handle assembly, an adapter assembly connected with the handle assembly, and a surgical end effector connected to the adapter assembly, in accordance with an embodiment of the present disclosure.

As illustrated in FIGS. 1A and 1B, hand-held electromechanical surgical instrument 10 includes a handle assembly 100 configured for selective connection with an adapter assembly 300, and, in turn, adapter assembly 300 is configured for selective connection with a surgical attachment, such as, for example, end effector 400 that is configured to perform various surgical functions. Handle assembly 100 is configured and adapted to actuate the various functions of end effector 400.

With reference to FIGS. 2-5, handle assembly 100 includes a handle housing 102 consisting of a body 104 and a handle portion 106 extending substantially perpendicularly from body 104. Body 104 of handle housing 102 has a plurality of motors M1, M2, M3 situated therein. Handle housing 102 includes a motor controller circuit board 112 coupled to the plurality of motors M1-M3, a first and second wireless modules 114, 116 (e.g., an RF module), and a flex circuit 118 interconnecting first and second wireless modules 114, 116 with motor controller circuit board 112.

First motor M1, second motor M2, and third motor M3 are each electrically connected (e.g., wirelessly connected) to motor controller circuit board 112 and a battery 142. Motors M1-M3 are disposed between first wireless module 114 and motor controller circuit board 112. Each motor M1-M3 includes a respective motor shaft 120a, 120b, 120c extending therefrom. Each motor shaft 120a-c has a tri-lobe transverse cross-sectional profile for transmitting rotative forces or torque.

Each motor M1-M3 is controlled by a respective motor controller (not explicitly shown). The motor controllers are disposed on motor controller circuit board 112 and may be A3930/31K motor drivers from Allegro Microsystems, Inc. The A3930/31K motor drivers are designed to control a 3-phase brushless DC (BLDC) motor with N-channel external power MOSFETs, such as motors M1-M3. Each of the motor controllers is coupled to second wireless module 116, which is disposed on first wireless module 114. Second wireless module 116 is also coupled to a memory, which is also disposed on first wireless module 114. Second wireless module 116 is an ARM Cortex M4 processor from Freescale Semiconductor, Inc, which includes 1024 kilobytes of internal flash memory. Second wireless module 116 communicates with the motor controllers through an FPGA, which provides control logic signals (e.g., coast, brake, etc.). The control logic of the motor controllers then outputs corresponding energization signals to their respective motors M1-M3 using fixed-frequency pulse width modulation (PWM).

Figure 3:
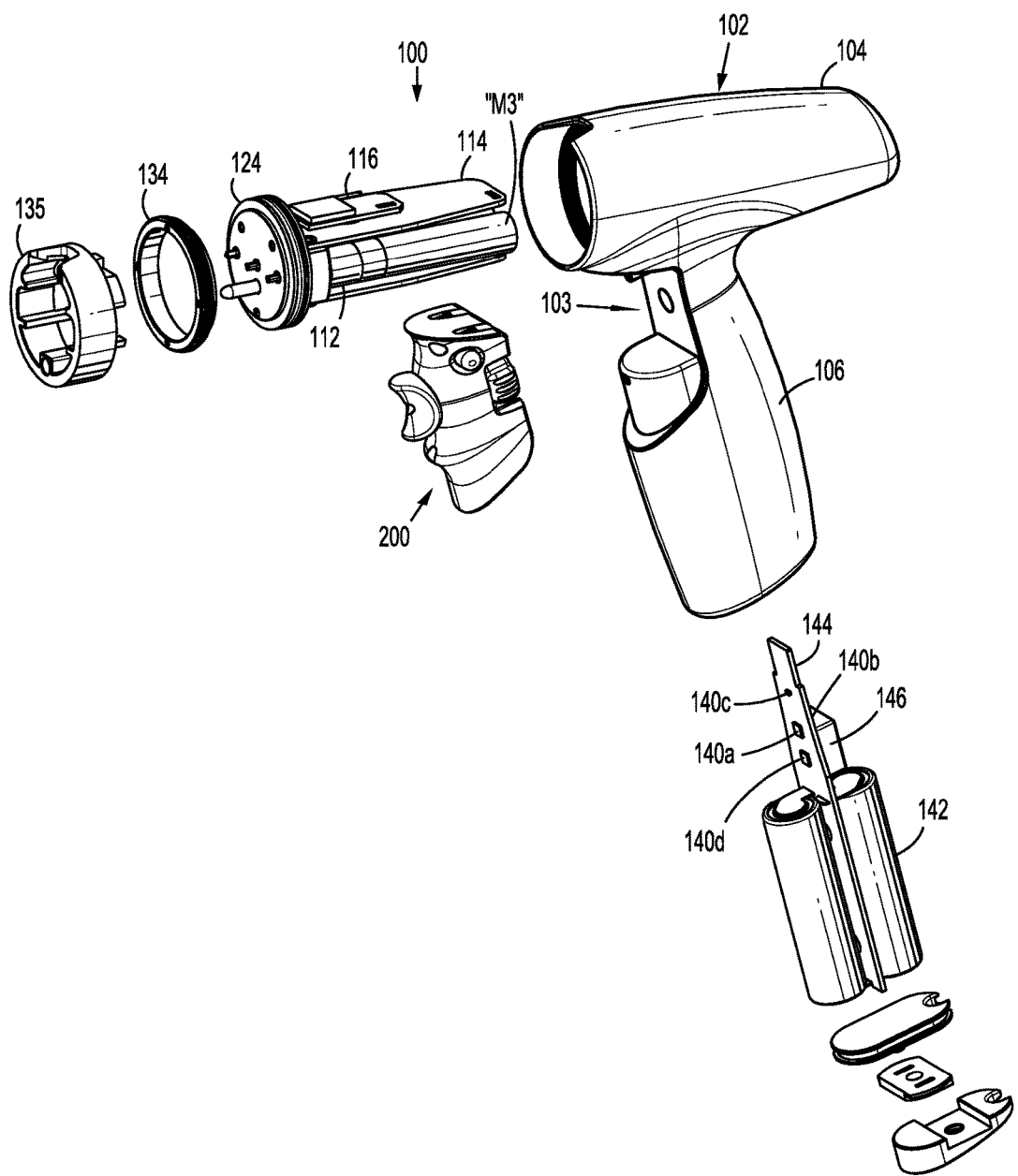
FIG. 3 is a perspective view, with parts separated, of components of the handle assembly of FIG. 1B.
Figure 4:
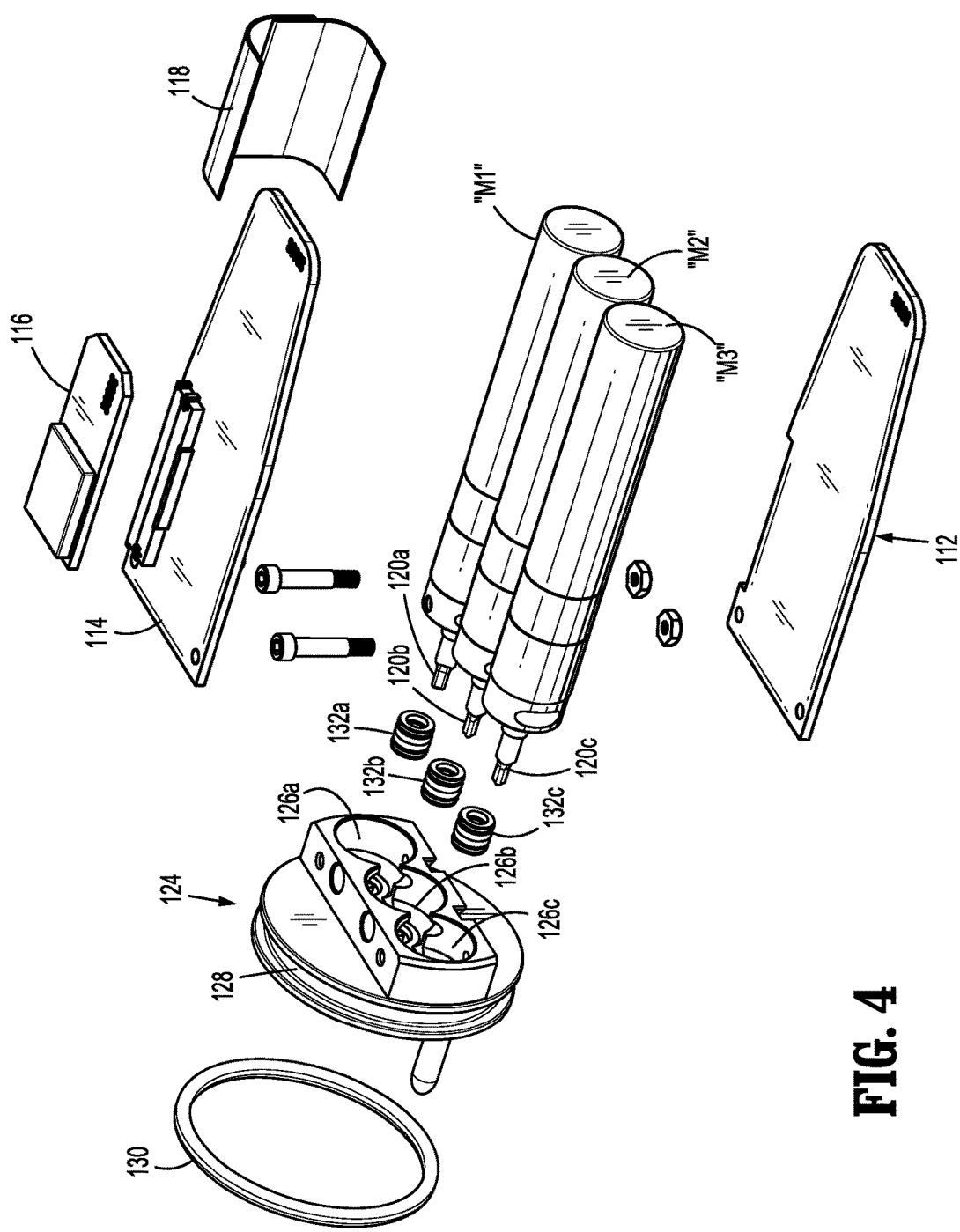
FIG. 4 is an exploded view of internal components of the handle assembly of FIG. 3.
Figure 5:
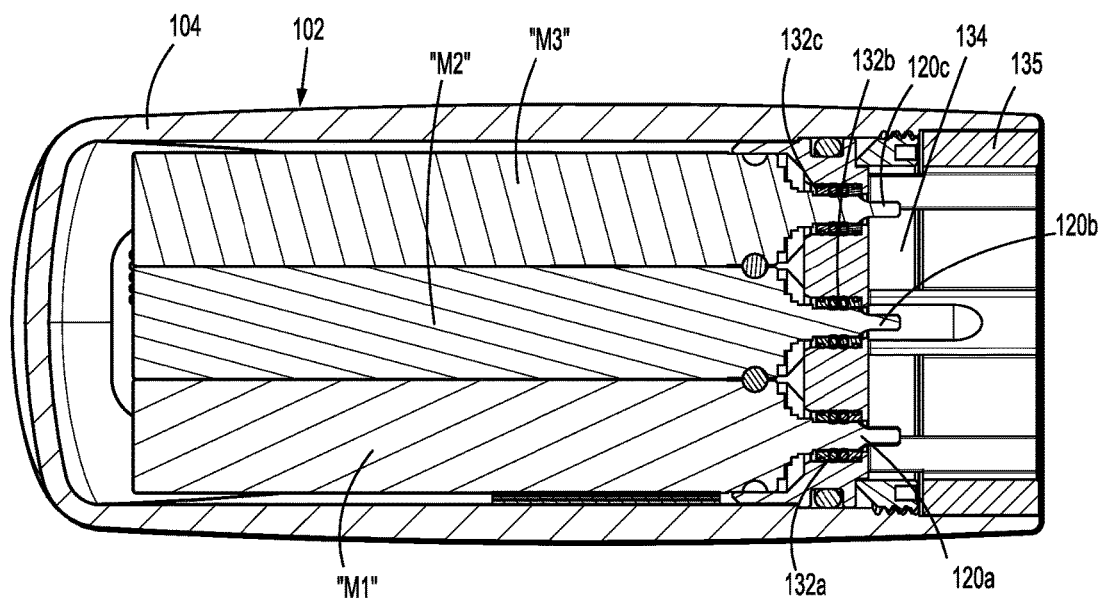
FIG. 5 is a cross-sectional view, taken along line 5-5 in FIG. 1B, illustrating three motors and various internal components of the handle assembly.

With reference to FIGS. 3-5, each motor M1-M3 is supported on a motor bracket, such as, for example, a motor mounting plate 124 such that motor shafts 120a-c are rotatably disposed within respective apertures 126a, 126b, 126c of motor mounting plate 124. Motor mounting plate 124 has a disc-shaped configuration and has a groove 128 defined in an outer circumferential surface thereof. Groove 128 is configured for receipt of an O-ring 130 therein to form a seal between motor mounting plate 124 and handle housing 102 upon assembly. Each motor shaft 120a-c has a seal, such as, for example, O-ring seals 132a, 132b, 132c disposed therearound, to prevent leaks between motor mounting plate 124 and motors M1-M3.

As illustrated in FIGS. 3 and 5, handle housing 102 includes a threaded mounting collar 134 configured to be threadedly engaged to an inner surface of handle housing 102 and in abutment with a distal side of mounting plate 124, such that mounting collar 134 prevents motor mounting plate 124 from moving distally within handle housing 102. Handle housing 102 further includes an inner housing 135 disposed in a distal portion of body 102, adjacent mounting collar 134. Inner housing 135 is configured for attachment of a proximal end of adapter assembly 300 (see FIG. 1A).

Motor shafts 120a-c of motors M1-M3 are non-rotatably received in respective drive connector sleeves (not shown) of adapter assembly 300. Rotation of motor shafts 120a-c by respective motors M1-M3 function to drive shafts and/or gear components of adapter assembly 300 (FIGS. 1A, 20, and 21) in order to perform the various operations of end effector 400. In particular, motors M1-M3 are configured to drive shafts and/or gear components of adapter assembly 300 in order to selectively actuate functions of end effector 400, for example, to articulate end effector 400 relative to adapter assembly 300, to rotate end effector 400 about a longitudinal axis "X" defined by adapter assembly 400 (FIG. 1A), to move a cartridge assembly 408 of end effector 400 relative to an anvil assembly 406 of end effector 400, and/or to fire staples from within cartridge assembly 408 of end effector 400.

Figure 2:
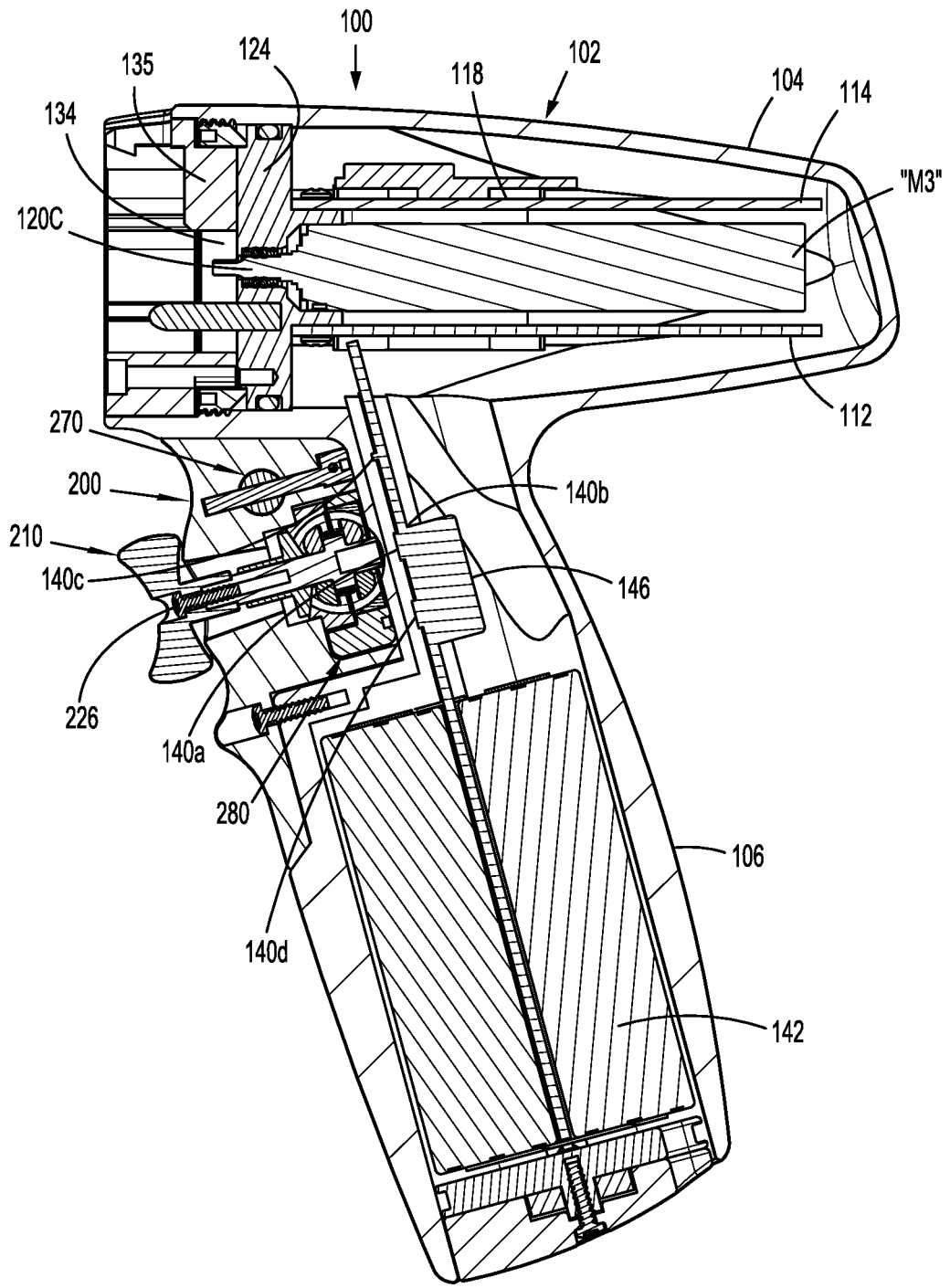
FIG. 2 is a cross-sectional view, taken along line 2-2 of FIG. 1B, of the handle assembly illustrating the internal components thereof.
Figure 6:
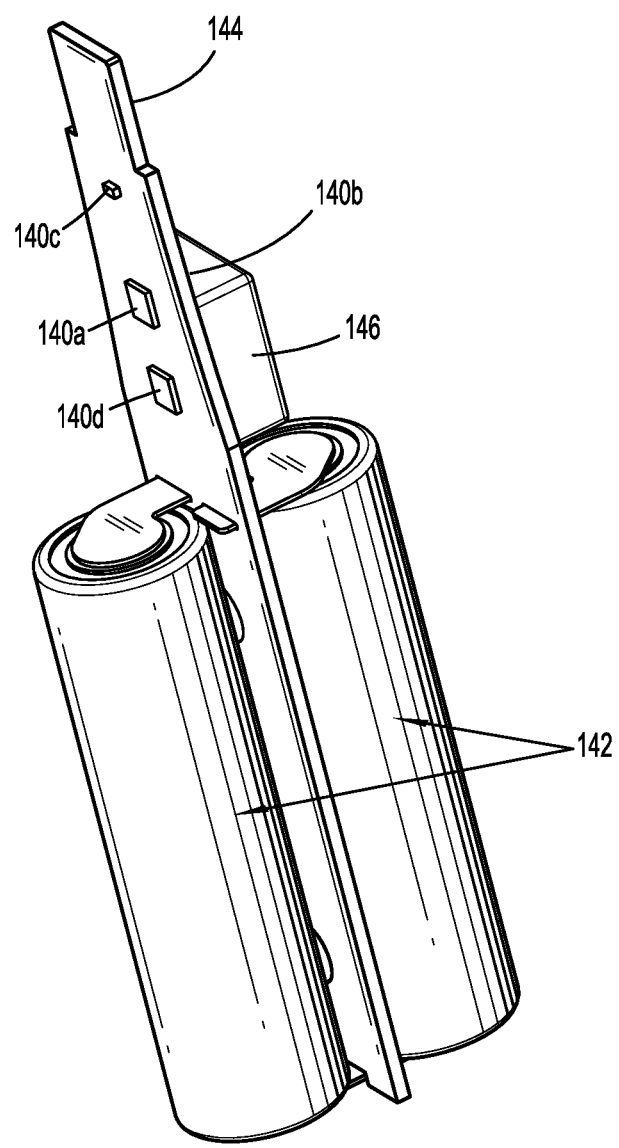
FIG. 6 is a perspective view of internal components of the handle assembly of FIG. 3 including a plurality of hall effect sensors and a battery.

With reference to FIGS. 2, 3 and 6, handle portion 106 of handle housing 102 has a plurality of hall effect sensors 140a, 140b, 140c, 140d and a battery 142 situated therein. Hall effect sensors 140a-d sense a movement of magnets of various switches of a switch assembly 200 (FIG. 10) to control the operation of each motor M1-M3 and, in turn, the functions of end effector 400, as described in detail below. Hall effect sensors 140a-d are in communication (e.g., via a wireless connection) with motor controller circuit board 112 to signal to motor controller circuit board 112 that motors M1-M3 are to be actuated.

Hall effect sensors 140a-d are arranged along a printed circuit board 144 situated within handle housing 102. Printed circuit board 144 has battery 142 mounted thereto that supplies power to motors M1-M3. An inductor 146 is connected to printed circuit board 144 and is configured to wirelessly transmit power generated by battery 142 to any of the electrical components of surgical instrument 10, including motors M1-M3, to drive the operation of end effector 400. For example, battery 142, via inductor 146, transmits power to motors M1-M3 by one of direct induction or resonant magnetic induction. In some embodiments, battery 142 may be physically connected to motors M1-M3 using wires. It is contemplated that more or less than four hall effect sensors may be supported on printed circuit board 144.

Figure 7B:
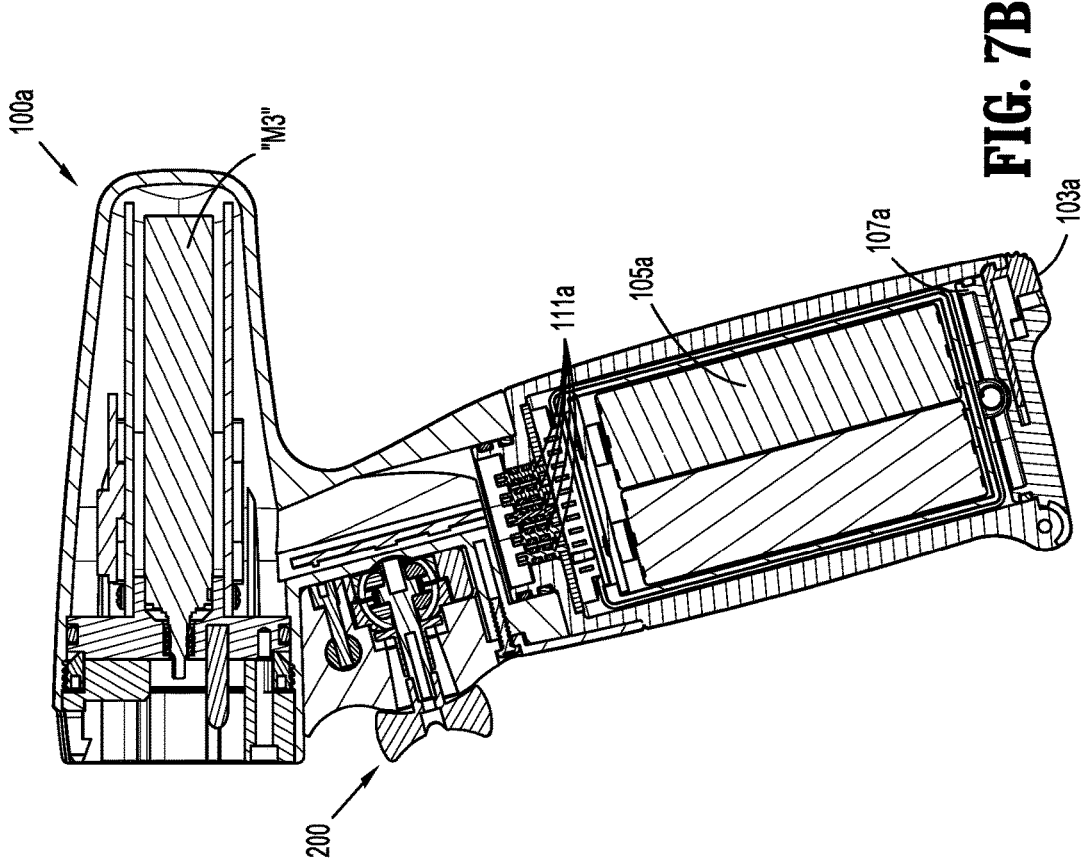
FIG. 7B is a cross-sectional view, taken along line 7B-7B of FIG. 7A, of the handle assembly.
Figure 7A:
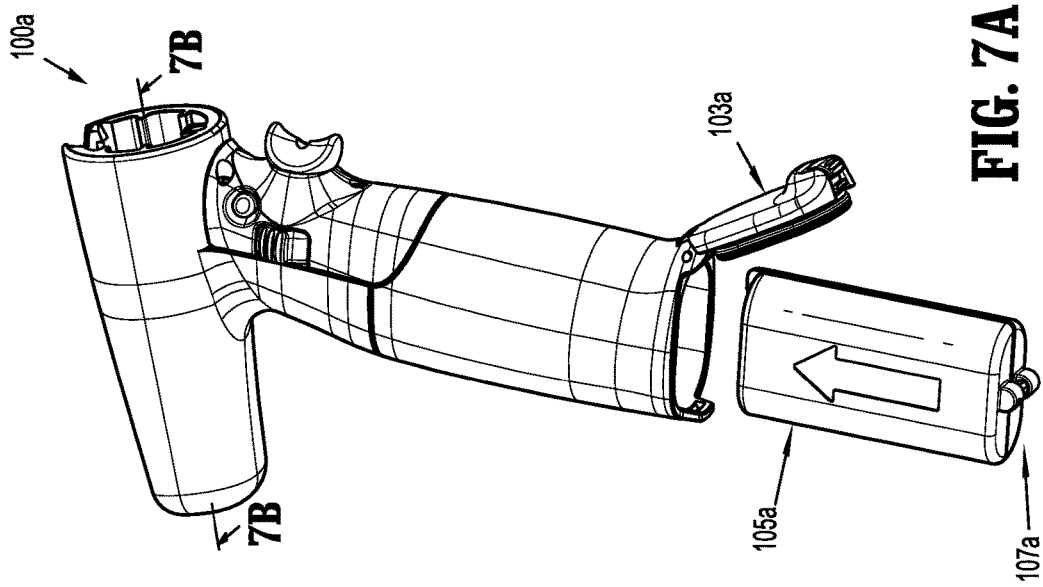
FIG. 7A is a perspective view of an embodiment of a handle assembly illustrating a removable battery.

Briefly, with reference to FIGS. 7A, 7B, 8A, 8B, and 9A-9D, alternative embodiments of handle assembly 100 are provided that may include similar components as handle assembly 100. Specifically, in one embodiment, as shown in FIGS. 7A and 7B, a handle assembly 100a, similar to handle assembly 100 has a door latch 103a that opens for reception or removal of a battery 105a and closes to selectively retain battery 105a in handle assembly 100a. Battery 105a has a spring loaded tab 107a and door latch 103a communicates with tab 107a of battery 105a. Upon receipt of battery 105a in handle assembly 100a, seals 111a of battery 105a prevent moisture from passing to the interior of handle assembly 100a.

Figure 8B:
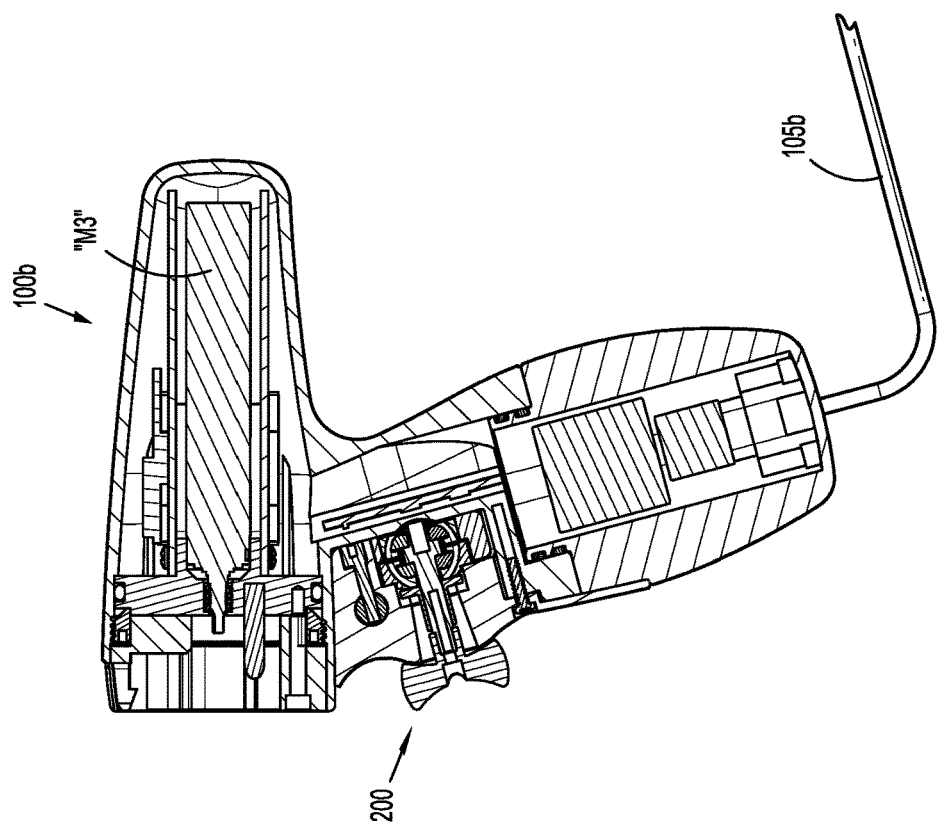
FIG. 8B is a cross-sectional view, taken along line 8B-8B of FIG. 8A, of the handle assembly.
Figure 8A:
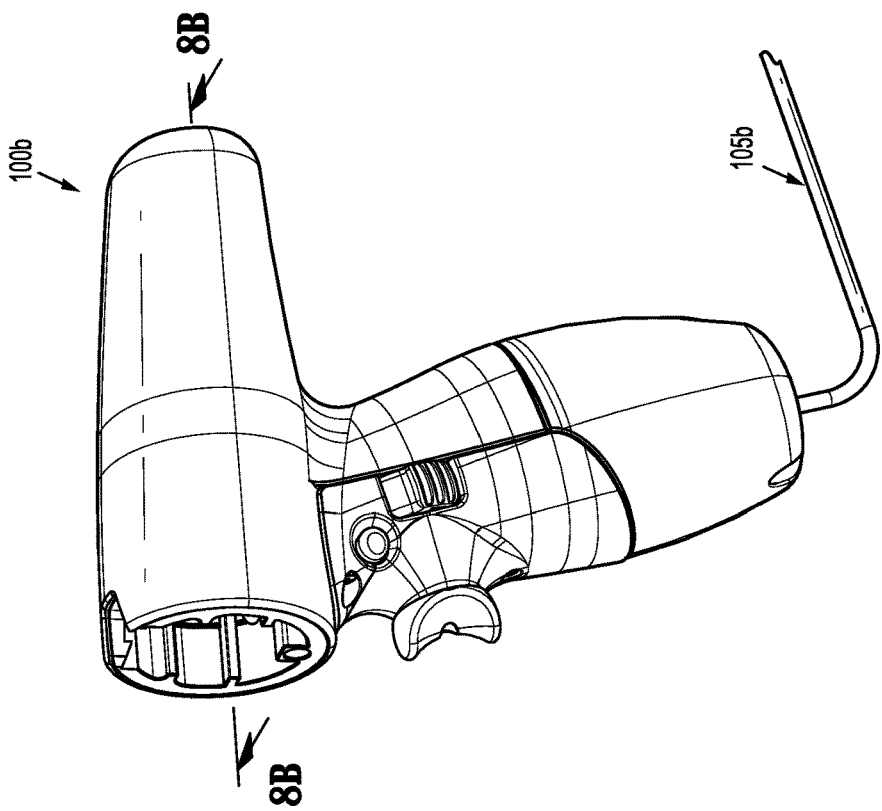
FIG. 8A is a perspective view of an embodiment of a handle assembly having a power cord.

In another embodiment, as shown in FIGS. 8A and 8B, a handle assembly 100b, similar to handle assembly 100 has an electric cord 105b coupled to motors M1-M3. Electric cord 105b is configured to be connected to a power source. As such, in the embodiment illustrated in FIGS. 8A and 8B, a battery is not required to drive the operation of motors M1-M3.

In yet another embodiment, as shown in FIGS. 9A-9D, a handle assembly 100c, similar to handle assembly 100 includes a power-pack 101c and an outer shell housing 102c configured to selectively receive and encase power-pack 101c. Outer shell housing 102c includes a distal half-section 104c and a proximal half-section 106c pivotably connected to distal half-section 104c by a hinge 108c located along an upper edge of distal half-section 104c and proximal half-section 106c. When joined, distal and proximal half-sections 104c, 106c define a shell cavity 110c therein in which power-pack 101c is selectively situated. Distal and proximal half-sections 104c, 106c include a snap closure feature 112c for selectively securing half-sections 104c, 106c to one another and for maintaining shell housing 102c in a closed condition.

Figure 9A:
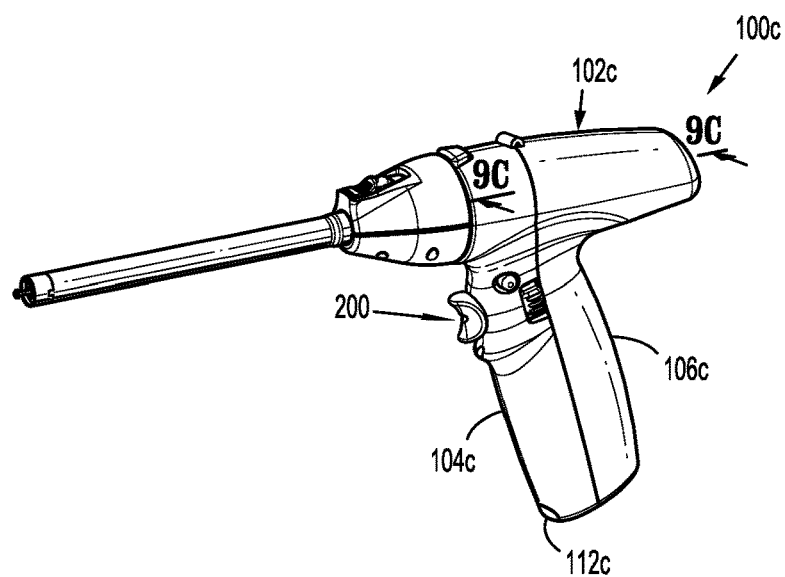
FIG. 9A is a perspective view of another embodiment of a hand-held surgical instrument illustrating a handle assembly thereof in a closed configuration.
Figure 9B:
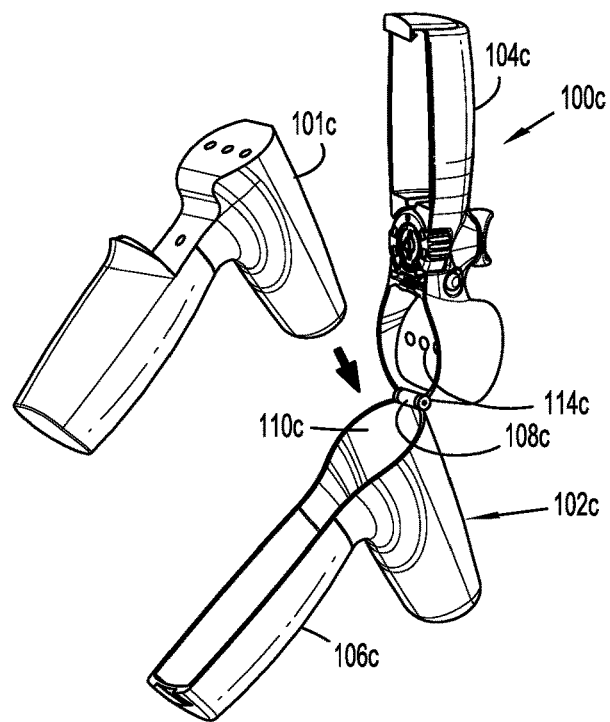
FIG. 9B is a perspective view of the handle assembly of FIG. 9A illustrating the handle assembly in an open configuration.
Figure 9C:
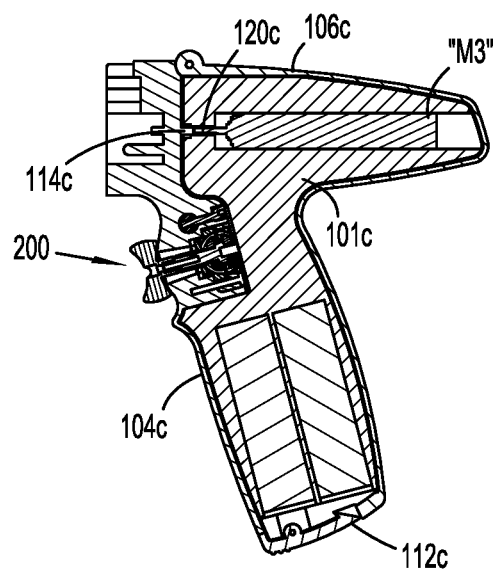
FIG. 9C is a cross-sectional view, taken along line 9C-9C, of the handle assembly.
Figure 9D:
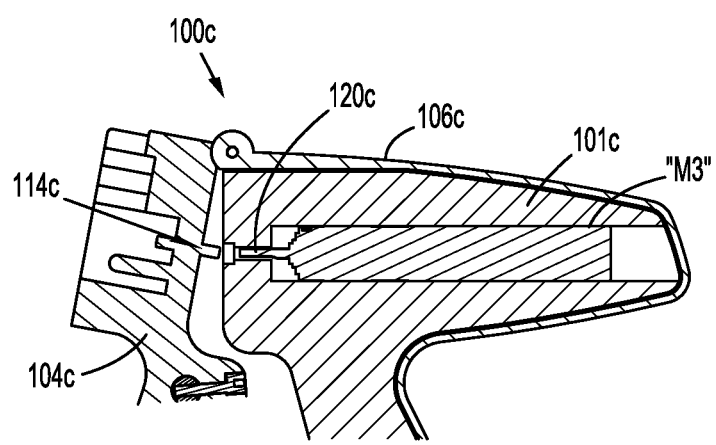
FIG. 9D is an enlarged view of the handle assembly of FIG. 9C with the handle assembly in a semi-open configuration.

With reference to FIGS. 9C and 9D, distal half-section 104c of shell housing 102c defines a connecting portion 114c configured to interconnect motors M1-M3 with drive shafts of adapter assembly 300 (FIGS. 1A, 20, and 21) upon joining of half-sections 104c, 106c.

With reference to FIGS. 10-19, a switch assembly 200 is provided to actuate functions of end effector 400 (FIG. 22). Any one of handle assemblies 100, 100a, 100b, 100c disclosed herein may be provided with switch assembly 200. For example, handle assembly 100 may have switch assembly 100 supported on handle housing 102. Switch assembly 200 includes a plurality of switch subassemblies 210, 270, 280 in operative mechanical and/or electrical communication with motors M1-M3, via hall effect sensors 140a-c. As such, when a user actuates one of the plurality of switch subassemblies 210, 270, 280, a respective one of motors M1-M3 is activated and, in turn, actuates a function performed by end effector 400 that is assigned to that switch subassembly 210, 270, 280 being actuated, as described in greater detail below.

Switch assembly 200 includes a switch housing 202, a first switch subassembly 210, a second switch subassembly 270, and a third switch subassembly 280. Switch housing 202 is received in a cavity 103 (FIG. 3) formed in handle housing 102. Switch housing 202 has an ergonomic design suitable for hand actuation of switch subassemblies 210, 270, 280. Switch housing 202 defines a vertical axis "Y," and defines a first channel 204 extending transversely therethrough. First channel 204 has a substantially tubular configuration adapted to retain components of first switch subassembly 210 therein.

First switch subassembly 210 is configured to actuate at least two functions of end effector 400, such as, for example: (i) clamping/firing and unclamping; and (ii) articulation of end effector 400. First switch subassembly 210 generally includes a toggle button 212 connected to a shaft 214 such that upon movement of shaft 214, via finger actuation of toggle button 212, a function of end effector 400 is actuated.

With reference to FIGS. 10-16, shaft 214 of first switch subassembly 210 is disposed within first channel or passage 204 of switch housing 202. Shaft 214 has a proximal end portion 216a and a distal end portion 216b. A magnet 218 is incorporated with or attached to a proximal-most end of proximal end portion 216a of shaft 214 such that upon assembly of switch assembly 200 with handle housing 102, magnet 218 is adjacent to first and second hall effect sensors 140a, 140b (see FIG. 2). Proximal end portion 216a of shaft 214 also has a substantially spherical or disc-shaped portion 220 to facilitate movement (e.g., rotation) of shaft 214 within first channel 204 of switch housing 202, as will be described in greater detail below. A first protrusion 222a extends or projects from a first, planar surface 224a of spherical portion 220, and a second protrusion 222b extends or projects from a second, planar surface 224b of spherical portion 220, opposite first planar surface 224a. Protrusions 222a, 222b are configured for rotatable connection with a respective keyed member 258a, 258b of first switch subassembly 210, as described in greater detail below.

Distal end portion 216b of shaft 214 has a non-circular cross-sectional profile corresponding to a non-circular receiving portion of toggle button 212 such that distal end portion 216b of shaft 214 non-rotatably couples to a proximal side of toggle button 212. A fastener, such as, for example, a screw 226 (FIG. 2), connects toggle button 212 to distal portion 216b of shaft 214. Toggle button 212 has a crescent-shaped configuration to enable a user's finger to move toggle button 212 at least along a first axis and a second axis, as shown in FIG. 11.

With specific reference to FIGS. 13-16, first switch subassembly 210 includes an outer member 228 and an inner member 230 non-rotatably disposed within outer member 228. Outer member 228 is disposable within first channel 204 of switch housing 202. Outer member 228 has a generally non-uniform cylindrical passageway extending therethrough. In particular, outer member 228 defines a first passageway 232 and a second passageway 234 in communication with first passageway 232. First passageway 232 has a first diameter and second passageway 234 has a second diameter, smaller than the first diameter of first passageway 232. Second passageway 234 has a substantially half-spherical configuration for reasons described below.

Outer member 228 has a proximal end portion 236a that defines the first passageway 232 therein, and a distal end portion 236b that defines the second passageway 234 therein. Proximal end portion 236a of outer member 228 defines a pair of opposing cutouts 238a, 238b therein. Cutouts 238a, 238b have a substantially squared configuration for receipt of tabs 252a, 252b of inner member 230.

Distal end portion 236b of outer member 228 has a pair of tabs 240a, 240b extending radially outwardly therefrom on opposite sides of outer member 228. Tabs 240a, 240b of outer member 228 are in alignment with respective cutouts 238a, 238b of proximal end portion 236a of outer member 228. Tabs 240a, 240b are configured to abut a stepped portion 208 (FIG. 12) of switch housing 202 that extends into first channel 204 to prevent outer member 228 from moving distally within first channel 204. Each tab 240a, 240b defines a notch 242a, 242b therein in communication with second passageway 234 and respective cutouts 238a, 238b of proximal end portion 236a. Notches 242a, 242b are configured for receipt of projections 262a, 262b of respective keyed members 258a, 258b. Notches 242a, 242b have a curvature, as shown in FIG. 15, corresponding to a curvature of projections 262a, 262b of respective keyed members 258a, 258b to enhance rotation of projections 262a, 262b of respective keyed members 258a, 258b therein, in directions indicated by arrows "A" in FIG. 15.

Distal end portion 236b of outer member 228 has a concave outer face 244 oriented distally and configured to engage a pivoting member 264 (FIGS. 10 and 12) of first switch subassembly 210. Outer face 244 of outer member 228 has a cutout 246 defined therein to allow shaft 214 to extend distally through outer member 228.

Inner member 230 of first switch subassembly 210 has a generally annular shape and defines a channel 248 therethrough. Channel 248 of inner member 230 has a substantially half-spherical configuration. The half-spherical configuration of second passageway 234 of outer member 228 and the half-spherical configuration of channel 248 of inner member 230 together define a cavity 250 having a substantially spherical configuration. Spherical portion 220 of shaft 214, and keyed members 258a, 258b are disposed in spherical cavity 250 and are rotatable therein such that outer member 228 and inner member 230 form a gimbal (or ball and socket joint) with shaft 14 and keyed members 258a, 258b.

Inner member 230 is configured for receipt within first passageway 232 of outer member 228 and to abut a ledge 243 of distal end portion 236b of outer member 228 to prevent inner member 230 from moving distally relative to outer member 228. Inner member 228 includes a pair of opposing tabs 252a, 252b extending radially outward therefrom. Upon assembly of inner member 230 within outer member 228, tabs 252a, 252b of inner member 230 are secured or disposed within cutouts 238a, 238b of outer member 230 to prevent inner member 230 from rotating relative to outer member 228. Each tab 252a, 252b of inner member 230 defines a notch 254a, 254b therein, similar to notches 242a, 242b of outer member 228. Notches 254a, 254b of inner member 230 are in communication with channel 248 of inner member 230. Notches 254a, 254b of inner member 230 are configured for receipt of projections 262a, 262b of respective keyed members 258a, 258b. Notches 254a, 254b of inner member 230 have a curvature, as shown in FIG. 15, corresponding to the curvature of projections 262a, 262b of respective keyed members 258a, 258b to permit rotation of projections 262a, 262b of respective keyed members 258a, 258b.

As mentioned above, first switch subassembly 210 includes keyed members 258a, 258b, which are rotatably connected to respective protrusions 222a, 222b of spherical portion 220 of shaft 214. Keyed members 258a, 258b, in combination with protrusions 222a, 222b, function to prevent shaft 214 from rotating within first channel 204 about a longitudinal axis defined along shaft 214. Each keyed member 258a, 258b has a generally hemi-spherical outer surface 260a, 260b and a projection 262a, 262b extending from respective hemi-spherical outer surface 260a, 260b. Projections 262a, 262b include a proximal tooth and a distal tooth each having an arcuate configuration. The proximal teeth of respective projections 262a, 262b are configured to be disposed in notches 254a, 254b of inner member 230 and distal teeth of respective projections 262a, 262b are configured to be disposed in notches 242a, 242b of outer member 228. Consequently, notches 242a, 242b of outer member 228 and notches 254a, 254b of inner member 230 resist and/or prevent keyed members 258a, 258b from moving in a lateral direction within cavity 250, and, in turn, prevent shaft 214 from rotating within first channel 204 about the longitudinal axis defined by shaft 214.

Figure 10:
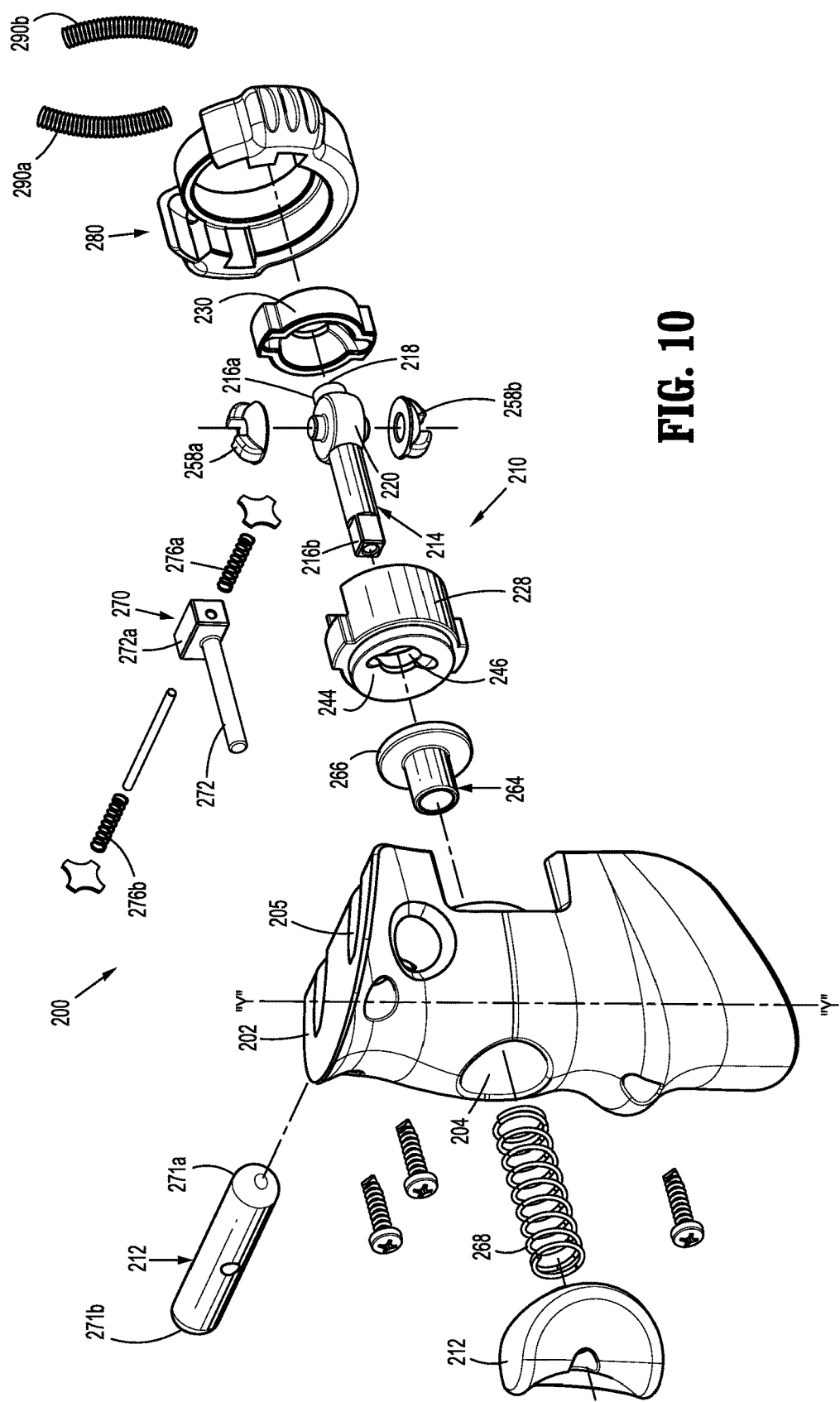
FIG. 10 is an exploded view of a switch assembly of the handle assembly of FIG. 1A.

With reference to FIGS. 10 and 12, first switch subassembly 210 further includes a pivoting member 264 disposed between outer member 228 and toggle button 212. Pivoting member 264 has a cone-shaped proximal end 266. Cone-shaped proximal end 266 abuts or seats within concave outer face 244 of outer member 228 such that pivoting member 264 is pivotable with respect to outer face 244 of outer member 228. A biasing member or spring 268 is disposed between cone-shaped proximal end 266 and toggle button 212 to bias toggle button 212 toward a position in which toggle button 212 is in line with first channel 204 of switch housing 202. As such, pivoting member 264 and biasing member 268 together act to maintain shaft 214 centrally disposed within first channel 204 of switch housing 202.

With continued reference to FIGS. 2 and 11-16, upon assembly and operation of first switch subassembly 210, toggle button 212 is actuated in one of an up-down direction, as indicated by arrows "C" in FIG. 11, or a left-right direction, as indicated by arrows "D" in FIG. 11. Upon toggle button 212 being moved in the up-down direction, shaft 214 rotates or pivots about a first pivot axis "E" as shown in FIG. 14. As shaft 214 pivots, magnet 218 disposed in proximal end 216a of shaft 214 moves relative to first hall effector sensor 140a, which is disposed adjacent proximal end 216a of shaft 214, to signal or change an intensity of a magnetic flux sensed by first hall effector sensor 140a. Upon first hall effect sensor 140a sensing movement of magnet 218 (i.e., change in the magnetic flux), as a result of pivoting of shaft 214 about the first pivot axis "E," first hall effector sensor 140a relays a message or signal to motor controller circuit board 112 (FIG. 4) to actuate first motor M1 to one of close jaw members 406, 408 of end effector 400 (i.e., execute a stapling or clamping function of end effector 400) or open jaw members 406, 408 of end effector 400.

Figure 20:
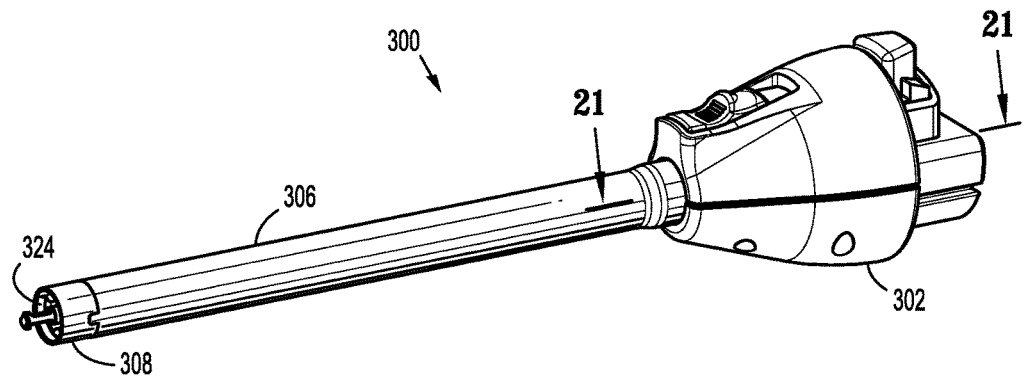
FIG. 20 is a perspective view of an adapter assembly of the hand-held electromechanical surgical instrument of FIG. 1A.
Figure 21:
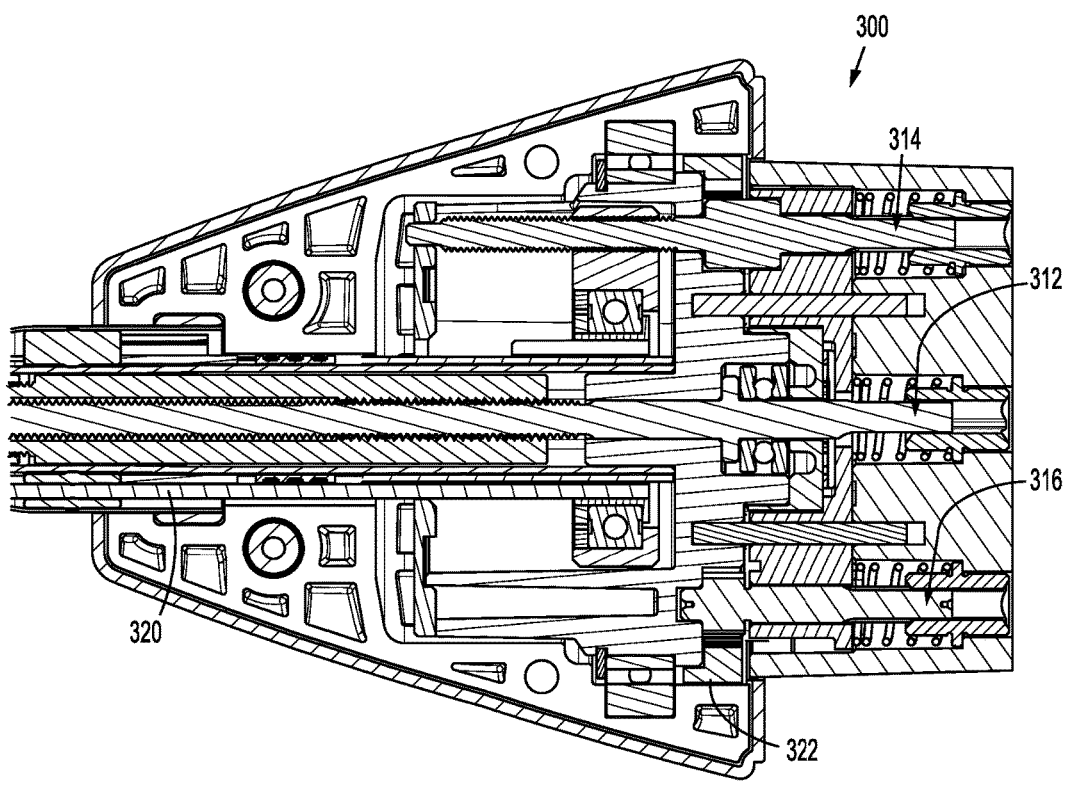
FIG. 21 is an enlarged cross-sectional view, taken along line 21-21 of FIG. 20, of the adapter assembly.

Upon toggle button 212 being moved in a left-right direction, as indicated by arrows "D" in FIG. 11, shaft 214 rotates or pivots about a second pivot axis "F" as shown in FIG. 14. As shaft 214 pivots, magnet 218 disposed in proximal end 216a of shaft 214 moves relative to second hall effector sensor 140b (FIG. 6) to signal or alter an intensity of a magnetic field sensed by second hall effect sensor 140b. Upon second hall effect sensor 140b sensing movement of magnet 218, as a result of rotation/pivoting of shaft 214 about the second pivot axis "F," second hall effect sensor 140b relays a message/signal to motor controller circuit board 112 to actuate second motor M2 to articulate end effector 400 (FIG. 22) relative to adapter assembly 300 (FIGS. 20 and 21). In some embodiments, rotation/pivoting of shaft 214 about the second pivot axis "F" is registered or sensed by first hall effect sensor 140a rather than second hall effect sensor 140b resulting in first hall effect sensor 140a relaying a message/signal to motor controller circuit board 112 to actuate second motor M2.

With reference to FIGS. 10-12 and 17, switch assembly 200 includes a second or safety switch subassembly 270 configured to selectively prevent a firing of end effector 400 from occurring (i.e., prevent staples from being ejected from cartridge assembly 408 upon a closing of jaw members 406, 408). As will be described in greater detail herein, when second switch subassembly 270 is in an unactuated or non-firing position, an actuation of first switch subassembly 210 will not result in a firing of end effector 400; however, when second switch subassembly 270 is in an actuated or firing position, an actuation of first switch subassembly 210 may result in a firing of end effector 400.

Second switch subassembly 270 includes a longitudinal safety bar 271 extending through a second channel 205 defined in switch housing 202. Second channel 205 is slidably disposed above or adjacent first channel 204, and extends transverse to longitudinal axis "Y" of switch housing 202 and longitudinal axis "X" of surgical instrument 10. Safety bar 271 has a first end 271a and a second end 271b and defines a longitudinal axis therebetween. First and second ends 271a, 271b protrude a distance from switch housing 202 such that first and second ends 271a, 271b of safety bar 271 can be actuated by a user's hand, for example, a finger or thumb.

Second switch subassembly 270 includes a post 272 extending centrally through safety bar 271, transversely thereto. Post 272 is fixed with safety bar 271 such that movement of safety bar 271 along the longitudinal axis thereof moves post 272 between a firing position and a non-firing position, as described in greater detail below. A proximal end 272a of post 272 includes a magnet 273 configured to communicate with third hall effect sensor 140c (FIGS. 2 and 6) disposed in handle portion 106 of handle housing 102.

Second switch subassembly 270 further includes a rod member 274 extending through proximal end 272a of post 272 and in parallel relation with safety bar 271. Rod 274 is fixedly secured to post 272 such that movement of safety bar 271 results in movement of rod 274. Rod 274 has a first end 274a in communication with a first dome switch 275a disposed in switch housing 202 and a second end 274b in communication with a second dome switch 275b disposed in switch housing 202. A first biasing member 276a is disposed between first dome switch 275a and proximal end 272a of post 272, and a second biasing member 276b is disposed between second dome switch 275b and proximal end 272a of post 272 to resiliently bias second switch subassembly 270 toward the non-firing position, in which first and second ends 274a, 274b of rod 274 are out of engagement with dome switches 275a, 275b. Dome switches 275a, 275b provide tactile feedback to a user upon transitioning second switch subassembly 270 between the non-firing and firing positions. In some embodiments, dome switches 275a, 275b are electrically connected to first motor M1 such that actuation of one of first and second dome switches 275a, 275b actuates first motor M1 or allows for actuation of first motor M1.

Figure 17:
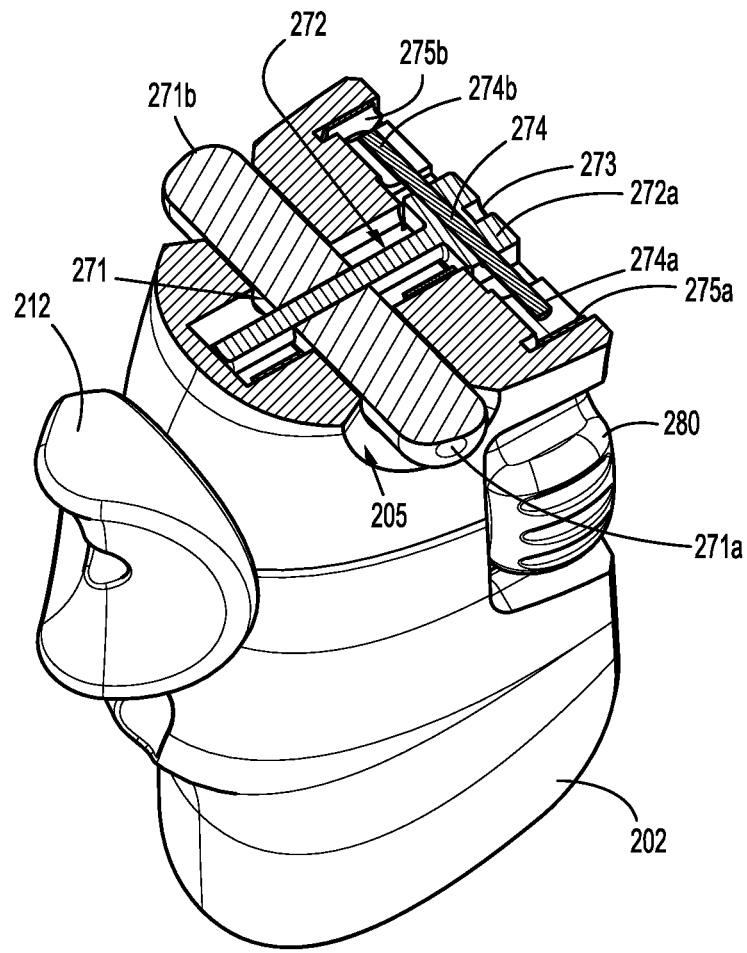
FIG. 17 is a top, cutaway view of the switch assembly of FIG. 11, illustrating a second switch subassembly.

With specific reference to FIG. 17, in assembly and operation of second switch subassembly 270, first or second ends 271a, 271b of safety bar 271 of second switch subassembly 270 is actuated, e.g., by a finger of a user, to translate safety bar 271 within second channel 205 of switch housing 202. Translation of safety bar 271 results in translation of post 272 via the fixed engagement between safety bar 271 and post 272. As post 272 translates within switch housing 202, magnet 273 of post 272 moves relative to third hall effect sensor 140c to signal or alter an intensity of a magnetic field sensed by third hall effector sensor 140c. Upon sensing movement of magnet 273, third hall effector sensor 140c relays the signal to a processor (not shown) that enables or disables an operation of first motor M1. With first motor M1 being enabled, via second switch subassembly 270 being in the firing position, an actuation of first switch subassembly 210 results in the firing of end effector 400. If first switch subassembly 210 is actuated without first or concurrently actuating second switch subassembly 270, first motor M1 will not function, and, in turn, a firing of end effector 400 will not occur.

In some embodiments, with second switch subassembly 270 in the non-firing position, first motor M1 may continue to cause a closing or opening of jaw members of end effector 400 without resulting in an ejection of staples from end effector 400. In some embodiments, handle assembly 100 may be configured such that an actuation of second switch subassembly 270 may deactivate first, second and/or third motors M1-M3.

Figure 19:
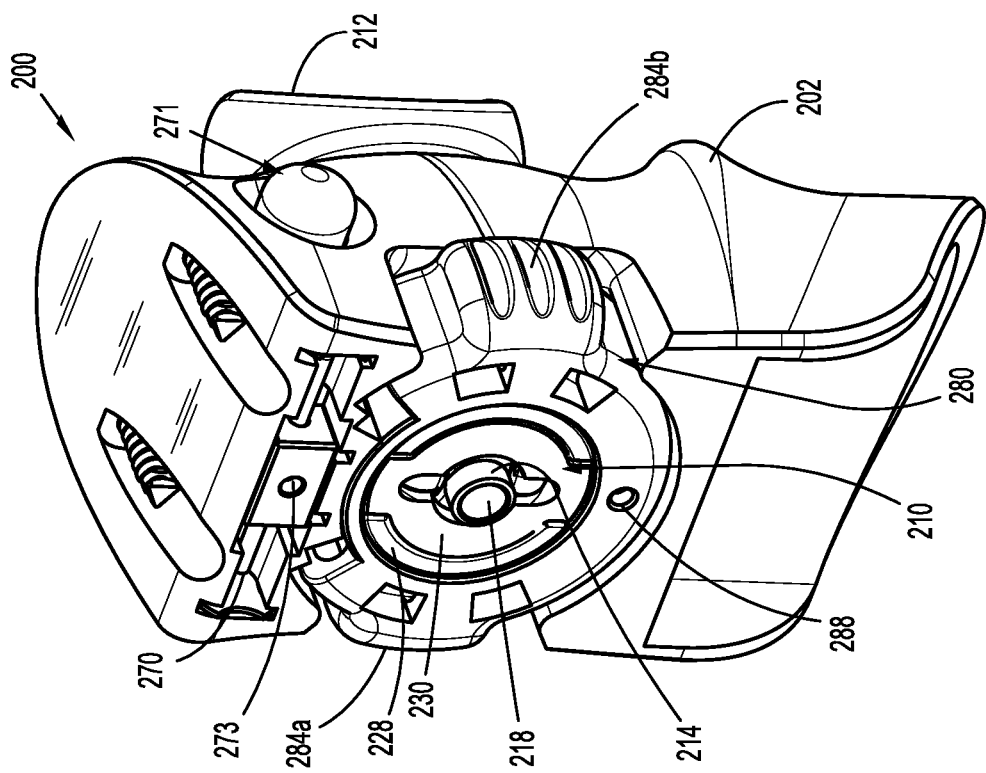
FIG. 19 is a proximal, perspective view of the switch assembly of FIG. 11.
Figure 18:
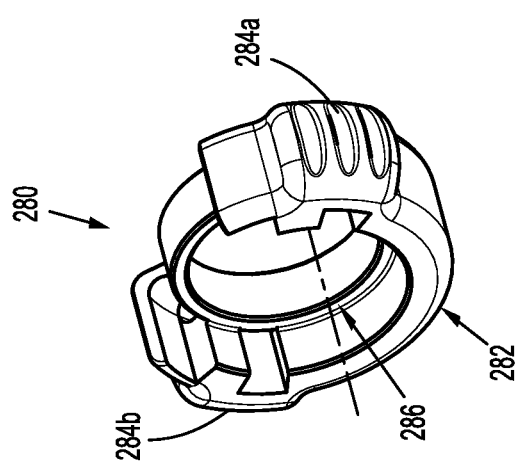
FIG. 18 is a perspective view of a third switch subassembly of the switch assembly of FIG. 10.

With reference to FIGS. 10, 18, and 19, switch assembly 200 further includes a third switch subassembly 280 configured to rotate end effector 400 about longitudinal axis "X" upon actuation of third switch subassembly 280. Third switch subassembly 280 includes an annular switch, such as, for example, a wheel or dial 282, rotatably disposed within switch housing 202. Wheel 282 has a pair of opposing lateral actuators 284a, 284b protruding from switch housing 202. Wheel 282 defines a channel 286 therein for rotatable disposal of outer and inner members 228, 230 of first switch subassembly 210. Wheel 282 is rotatable relative to the components of first switch subassembly 210. A magnet 288 is disposed within wheel 282, for example, in a bottom portion of wheel 282. Magnet 288 is disposed adjacent fourth hall effect sensor 140d (FIGS. 2 and 6) upon assembly of switch assembly 200 with handle housing 102. Third switch subassembly 280 includes a pair of biasing members 290a, 290b captured between switch housing 202 and wheel 282 to resiliently bias wheel 282 toward a non-actuated position.

In an assembly and operation of third switch subassembly 280, wheel 282 is rotated relative to switch housing 202 via actuation of lateral actuators 284a, 284b by, for example, a hand of a user. Rotation of wheel 282 moves magnet 288 of third switch subassembly 280 away from fourth hall effect sensor 140d (FIGS. 2 and 6) of surgical instrument 10 to signal or alter an intensity of a magnetic field sensed by fourth hall effector sensor 140d. Upon sensing movement of magnet 288, fourth hall effector sensor 140d relays the signal to motor controller circuit board 112 to actuate third motor M3 to rotate end effector 400.

In some embodiments, switch subassemblies 210, 270, 280 of switch assembly 200 may be assigned to actuate various functions to be carried out by various surgical end effectors. It is contemplated that the switch subassemblies 210, 270, 280 can be variously configured, such as, for example, as switches, rockers, flaps, latches, levers, dials, buttons, or touch screens.

With reference to FIGS. 20 and 21, adapter assembly 300 is configured to convert a rotation of either of motor shafts 120a-c of motors M1-M3 into actuation of components of end effector 400. Adapter assembly 300 includes a proximal end, such as, for example, an outer knob housing 302, and an outer tube 306 extending from a distal end of knob housing 302. Knob housing 302 and outer tube 306 are configured and dimensioned to house the components of adapter assembly 300. Outer tube 306 is dimensioned for endoscopic insertion, in particular, outer tube 306 is passable through a typical trocar port, cannula or the like. Knob housing 302 is dimensioned to not enter the trocar port, cannula of the like. Knob housing 302 is configured and adapted to be connected to inner housing 135 (FIG. 3) of handle housing 102 of handle assembly 100.

Adapter assembly 300 includes a first rotatable proximal drive shaft 312, a second rotatable proximal drive shaft 314, and a third rotatable proximal drive shaft 316 therein. Each proximal drive shaft 312, 314, 316 functions as a rotation receiving member to receive rotational forces from respective motor shafts 120a-c of handle assembly 100. Drive shafts 312, 314, 316 are components of respective force/rotation transmitting/converting assemblies, each disposed within outer tube 306. Each force/rotation transmitting/converting assembly is configured and adapted to transmit/convert a speed/force of rotation (e.g., increase or decrease) of first, second, and third motor shafts 120a-c of handle assembly 100 before transmission of such rotational speed/force to end effector 400.

Specifically, adapter assembly 300 includes a first, a second and a third force/rotation transmitting/converting assembly, respectively, disposed within outer tube 306. Each force/rotation transmitting/converting assembly is configured and adapted to transmit or convert a rotation of a first, second and third motor shafts 120a-c of handle assembly 100 into axial translation of an articulation bar 320 of adapter assembly 300, to effectuate articulation of end effector 400; a rotation of a ring gear 322 of adapter assembly 300, to effectuate rotation of adapter assembly 300 and, in turn, a rotation of end effector 400; or axial translation of a distal drive member 324 of adapter assembly 300 to effectuate closing, opening and firing of end effector 400.

As illustrated in FIGS. 1A and 22, end effector 400 is configured to be coupled to a distal end 308 of outer tube 306 of adapter assembly 300. End effector 400 includes a proximal body portion 402 and a tool assembly 404. Proximal body portion 402 is releasably attached to distal end 308 of adapter assembly 300 and tool assembly 404 is pivotally attached to a distal end of proximal body portion 402 of end effector 400. Proximal body portion 402 is configured to articulate relative to distal end 308 of adapter assembly 300. Tool assembly 404 includes an anvil assembly 406 and a cartridge assembly 408. Cartridge assembly 408 is pivotal in relation to anvil assembly 406 and is movable between an open or unclamped position and a closed or clamped position for insertion through a cannula of a trocar.

For a detailed discussion of the construction and operation of surgical end effector 400, as illustrated in FIGS. 1A and 22, reference may be made to U.S. Pat. No. 7,819,896, filed on Aug. 31, 2009, entitled "TOOL ASSEMBLY FOR A SURGICAL STAPLING DEVICE."

In operation, to open or close/fire end effector 400, toggle button 212 of first switch subassembly 210 is moved in an up-down direction. Magnet 218 disposed in proximal end 216a of shaft 214 moves relative to first hall effector sensor 140a to signal hall effector sensor 140a, as described above. First hall effector sensor 140a causes first motor M1 to actuate the first drive converting/transmitting assembly of adapter assembly 300, which in turn causes jaw members 406, 408 of end effector 400 to open/close and/or to fire staples into tissue.

To articulate end effector 400, toggle button 212 is moved in a left-right direction. Magnet 218 disposed in proximal end 216a of shaft 212 moves relative to second hall effector sensor 140b to signal hall effect sensor 140, as described above. Upon second hall effect sensor 140b sensing the movement of magnet 218, hall effect sensor 140b causes second motor M2 to actuate the second drive converting/transmitting assembly of adapter assembly 300, which, in turn, causes proximal body portion 402 of end effector 400 to articulate (i.e., pivot) relative to adapter assembly 300.

To carry out a rotation of end effector 400 about longitudinal axis "X," wheel 282 of third switch subassembly 280 is rotated relative to switch housing 202 via actuation of lateral actuators 284a, 284b. Rotation of wheel 282 moves magnet 288 of third switch subassembly 280 away from fourth hall effect sensor 140d of surgical instrument 10 to signal fourth hall effector sensor 140d, as described above. Upon sensing movement of magnet 288, fourth hall effector sensor 140d causes third motor M3 to actuate the third rotation converting/transmitting assembly of adapter assembly 300 thereby causing outer knob housing 302 of adapter assembly 300 to rotate. As outer knob housing 302 is rotated, outer tube 306 is caused to be rotated about longitudinal axis "X." As outer tube 306 is rotated, end effector 400, which is connected to distal end 308 of adapter assembly 300, is also caused to be rotated about longitudinal axis "X."

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments including switch assemblies. Therefore, the above description should not be construed as limiting, but merely as exemplifications of embodiments. Those skilled in the art will envision other modifications within the scope and spirit of the present disclosure.

What is claimed is:

1. A switch assembly for actuating functions of a handheld surgical instrument, comprising:
   a switch housing defining a channel;
   a first switch subassembly including:
      a shaft disposed within the channel of the switch housing, wherein the shaft is configured to pivot relative to the switch housing about a first pivot axis to actuate a first function of a surgical instrument, and a second pivot axis to actuate a second function of a surgical instrument; and
   an annular switch rotatably disposed within the switch housing to actuate at least one function of a surgical instrument.

2. A switch assembly for actuating functions of a handheld surgical instrument, comprising:
   a switch housing defining a channel; and
   a first switch subassembly including:
      a shaft disposed within the channel of the switch housing, wherein the shaft is configured to pivot relative to the switch housing about a first pivot axis to actuate a first function of a surgical instrument, and a second pivot axis to actuate a second function of a surgical instrument;

an inner member disposed within the channel of the switch housing, the inner member defining a spherical cavity therein, the shaft having a spherical proximal end portion disposed in the spherical cavity;

an outer member prevented from moving distally relative to the switch housing, the inner member being non-rotatably disposed within the outer member;

a pivoting member having a cone-shaped proximal end portion in abutment with a concave face of the outer member; and a biasing member disposed between the cone-shaped proximal end portion of the pivoting member and a toggle button to center the toggle button within the channel.

3. A switch assembly for actuating functions of a handheld surgical instrument, comprising:

a switch housing defining a channel; and a first switch subassembly including:
- a shaft disposed within the channel of the switch housing and having a spherical proximal end portion, the shaft being configured to pivot relative to the switch housing about at least one axis to actuate at least one function of a surgical instrument, wherein the spherical proximal end portion of the shaft is disposed in a spherical cavity in the switch housing;
- a first keyed member rotatably connected to the spherical proximal end portion of the shaft; and
- a second keyed member rotatably connected to the spherical proximal end portion of the shaft such that the first and second keyed members resist rotation of the shaft about a longitudinal axis defined by the shaft.

4. The switch assembly according to claim 3, wherein the shaft is configured to pivot relative to the switch housing about a first pivot axis to actuate a first function of a surgical instrument, and a second pivot axis to actuate a second function of a surgical instrument.

5. The switch assembly according to claim 3, wherein the first switch subassembly further includes an inner member disposed within the channel of the switch housing, the inner member defining the spherical cavity therein.

6. The switch assembly according to claim 5, wherein the first switch subassembly further includes a outer member prevented from moving distally relative to the switch housing, the inner member being non-rotatably disposed within the outer member.

7. The switch assembly according to claim 6, wherein the shaft of the first switch subassembly extends through the inner and outer members.

8. The switch assembly according to claim 6, wherein the inner and outer members cooperatively define the spherical cavity.

9. A switch assembly for actuating functions of a handheld surgical instrument, comprising:

a switch housing defining a channel;

a first switch subassembly having a shaft disposed within the channel of the switch housing, wherein the shaft is configured to pivot relative to the switch housing about a first pivot axis to actuate a first function of a surgical instrument, and a second pivot axis to actuate a second function of a surgical instrument; and a second switch subassembly including:
- a safety bar extending through the switch housing, transverse to a longitudinal axis defined by the switch housing, the safety bar being axially movable in the switch housing; and
- a post extending through the safety bar, transversely thereto, such that movement of the safety bar along a longitudinal axis defined by the safety bar moves the post between a firing position and a non-firing position.

10. The switch assembly according to claim 9, wherein a proximal end portion of the post of the second switch subassembly includes a magnet configured to communicate with a hall effect sensor of a surgical instrument.

11. The switch assembly according to claim 9, further comprising a third switch subassembly including an annular switch rotatably disposed within the switch housing to actuate at least one function of a surgical instrument.

12. The switch assembly according to claim 9, wherein the shaft includes a proximal end portion having a sensing element or a sensed element.

13. The switch assembly according to claim 12, wherein the sensing element is a hall effect sensor and the sensed element is a magnet.

14. The switch assembly according to claim 12, wherein the first switch subassembly further includes a toggle button non-rotatably connected to a distal end portion of the shaft.

15. The switch assembly according to claim 9, wherein the first switch subassembly further includes an inner member disposed within the channel of the switch housing, the inner member defining a spherical cavity therein, the shaft having a spherical proximal end portion disposed in the spherical cavity.

16. The switch assembly according to claim 15, wherein the first switch subassembly further includes:
- a first keyed member rotatably connected to the spherical proximal end portion of the shaft; and
- a second keyed member rotatably connected to the spherical proximal end portion of the shaft such that the keyed members resist rotation of the shaft about a longitudinal axis defined by the shaft.

17. The switch assembly according to claim 15, wherein the first switch subassembly further includes an outer member prevented from moving distally relative to the switch housing, the inner member being non-rotatably disposed within the outer member.

18. The switch assembly according to claim 17, wherein the first switch subassembly further includes:
- a pivoting member having a cone-shaped proximal end portion in abutment with a concave face of the outer member; and
- a biasing member disposed between the cone-shaped proximal end portion of the pivoting member and a toggle button to center the toggle button within the channel.

19. The switch assembly according to claim 17, wherein the inner and outer members cooperatively define the spherical cavity.

20. The switch assembly according to claim 17, wherein the shaft of the first switch subassembly extends through the inner and outer members.

* * * * *